US008492347B2

(12) United States Patent
Hahn et al.

(10) Patent No.: US 8,492,347 B2
(45) Date of Patent: Jul. 23, 2013

(54) PEPTIDE FOR INDUCTION OF IMMUNE TOLERANCE AS TREATMENT FOR SYSTEMIC LUPUS ERYTHEMATOSUS

(75) Inventors: Bevra H. Hahn, Encino, CA (US); Fanny M. Ebling, Encino, CA (US); Antonio La Cava, Santa Monica, CA (US); Ram Raj Singh, Los Angeles, CA (US); Ram Pyare Singh, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 540 days.

(21) Appl. No.: 12/682,759

(22) PCT Filed: Oct. 17, 2008

(86) PCT No.: PCT/US2008/080356
§ 371 (c)(1),
(2), (4) Date: Apr. 12, 2010

(87) PCT Pub. No.: WO2009/052415
PCT Pub. Date: Apr. 23, 2009

(65) Prior Publication Data
US 2010/0234302 A1    Sep. 16, 2010

Related U.S. Application Data

(60) Provisional application No. 60/999,289, filed on Oct. 17, 2007.

(51) Int. Cl.
*A61K 38/10* (2006.01)
*A61K 38/00* (2006.01)
*A61K 38/04* (2006.01)
*G01N 33/00* (2006.01)
*C07K 5/00* (2006.01)
*C07K 7/00* (2006.01)
*C07K 16/00* (2006.01)
*C07K 17/00* (2006.01)

(52) U.S. Cl.
USPC ............................ 514/21.5; 435/7.24; 530/326

(58) Field of Classification Search
None
See application file for complete search history.

(56) References Cited

U.S. PATENT DOCUMENTS

| 7,081,242 | B1 | 7/2006 | Linnik et al. | |
|---|---|---|---|---|
| 7,135,457 | B1 | 11/2006 | Alvarez et al. | |
| 7,501,132 | B2 | 3/2009 | Ades et al. | |
| 2004/0014652 | A1* | 1/2004 | Trouet et al. | 514/12 |
| 2006/0269553 | A1* | 11/2006 | Kim et al. | 424/155.1 |
| 2007/0086942 | A1 | 4/2007 | Chang et al. | |
| 2010/0234302 | A1 | 9/2010 | Hahn et al. | |
| 2011/0028409 | A1 | 2/2011 | Pratesi et al. | |

OTHER PUBLICATIONS

Sela et al. Different roles of D-amino acids in immune phenomena. FASEB. 1997, vol. 11, pp. 449-456.*
PCT/US2008/80356 International Search Report and Written Opinion.
Celine Adessie and Claudio Soto, "Converting a peptide into a Drug: Strategies to Improve Stability and Bioavailability",Current Medicinal Chemistry, 2002, 9, 963-978.
Antonio La Cava et al., "Ig-Reactive CD4+CD25+ T Cells from Tolerized (New Zealand Black X new Zealand White)F1 Mice Suppress In Vitro Production of Antibodies to DNA1", The Journal of Immunology, 2004.
Bevra H. Hahn et al., "Treatment With a Consensus Peptide Based on Amino Acid Sequences in Autoantibodies Prevents T Cell Activation by Autoantigens and Delays Disease Onset in Murine Lupus", Arthritis & Rheumatism, vol. 44, No. 2, Feb. 2001, pp. 432-441.
Bevra H. Hahn et al., "Tolerogenic Treatment of Lupus Mice with Consensus Peptide Induces Foxp3-Expressing, Apoptosis-Resistant, TGF B-Secreting CD8+ T Cell Suppressors1", The Journal of Immunology, 2005.
International Search Report for PCT Application No. PCT/US2012/026364 filed on Feb. 23, 2012.

* cited by examiner

*Primary Examiner* — Marcela M Cordero Garcia
(74) *Attorney, Agent, or Firm* — Gates & Cooper LLP

(57) ABSTRACT

The present invention relates to D-amino acid peptides and their use in methods for the diagnosis and/or treatment of immune disorders such as systemic lupus erythematosus.

20 Claims, 10 Drawing Sheets

SEQUENCE LISTING

```
<160> NUMBER OF SEQ ID NOS: 19

<210> SEQ ID NO 1
<211> LENGTH: 15
<212> TYPE: PRT
<213> ORGANISM: Artificial Sequence
<220> FEATURE:
<223> OTHER INFORMATION: Consensus sequence derived from Mus musculus

<400> SEQUENCE: 1

Phe Ile Glu Trp Asn Lys Leu Arg Phe Arg Gln Gly Leu Glu Trp
1               5                   10                  15

<210> SEQ ID NO 2
<211> LENGTH: 23
<212> TYPE: DNA
<213> ORGANISM: Artificial Sequence
<220> FEATURE:
<223> OTHER INFORMATION: Primer
```

-continued

<400> SEQUENCE: 2
acccacttcc cagtcggcca gag                                    23

<210> SEQ ID NO 3
<211> LENGTH: 15
<212> TYPE: PRT
<213> ORGANISM: Mus musculus

<400> SEQUENCE: 3

Ala Ile Ala Trp Ala Lys Ala Arg Ala Arg Gln Gly Leu Glu Trp
 1               5                  10                  15

<210> SEQ ID NO 4
<211> LENGTH: 15
<212> TYPE: PRT
<213> ORGANISM: Mus musculus

<400> SEQUENCE: 4

Gly Tyr Phe Met Asn Trp Val Lys Gln Ser His Gly Lys Ser Leu
 1               5                  10                  15

<210> SEQ ID NO 5
<211> LENGTH: 12
<212> TYPE: PRT
<213> ORGANISM: Mus musculus

<400> SEQUENCE: 5

Met Asn Trp Val Lys Gln Ser His Gly Lys Ser Leu
 1               5                  10

<210> SEQ ID NO 6
<211> LENGTH: 12
<212> TYPE: PRT
<213> ORGANISM: Mus musculus

<400> SEQUENCE: 6

Phe Tyr Asn Gln Lys Phe Lys Gly Lys Ala Thr Leu
 1               5                  10

<210> SEQ ID NO 7
<211> LENGTH: 20
<212> TYPE: PRT
<213> ORGANISM: Mus musculus

<400> SEQUENCE: 7

Thr Gly Tyr Tyr Met Gln Trp Val Lys Gln Ser Pro Glu Lys Ser Leu
 1               5                  10                  15

Glu Trp Ile Gly
             20

<210> SEQ ID NO 8
<211> LENGTH: 15
<212> TYPE: PRT
<213> ORGANISM: Mus musculus

<400> SEQUENCE: 8

Val Lys Gln Arg Pro Gly His Gly Leu Glu Trp Ile Gly Glu Ile
 1               5                  10                  15

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
tgagacagaa gttctgggct tct                                    23

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
caagatgcag tgtgtagcgt tca                                    23

<210> SEQ ID NO 11
<211> LENGTH: 26
<212> TYPE: DNA
<213> ORGANISM: Artificial Sequence
<220> FEATURE:
<223> OTHER INFORMATION: Primer

<400> SEQUENCE: 11
tcctgcggcc tagctctgag atamra                                 26

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
cagccgggaa gacaataact g                                      21

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ccgcagctct aggagcatgt                                        20

<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
aaacggaagc gcatcgaa                                          18

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gggactggcg agccttagtt                                        20

<210> SEQ ID NO 16
<211> LENGTH: 28

```
<212> TYPE: DNA
<213> ORGANISM: Artificial Sequence
<220> FEATURE:
<223> OTHER INFORMATION: Primer

<400> SEQUENCE: 16
ccatccgtgg ccagatcctg tcctamra                                              28

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
tgcagggcag ctaggtactt gta                                                   23

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
tctcggagat cccctttgtc t                                                     21

<210> SEQ ID NO 19
<211> LENGTH: 29
<212> TYPE: DNA
<213> ORGANISM: Artificial Sequence
<220> FEATURE:
<223> OTHER INFORMATION: Primer

<400> SEQUENCE: 19
tccgaacagc atcatccttc ttagcatcc                                             29
```

PEPTIDE FOR INDUCTION OF IMMUNE TOLERANCE AS TREATMENT FOR SYSTEMIC LUPUS ERYTHEMATOSUS

REFERENCE TO RELATED APPLICATIONS

This application claims priority under Section 119(e) from U.S. Provisional Application Ser. No. 60/999,289 filed Oct. 17, 2007, the contents of which are incorporated herein by reference.

STATEMENT OF GOVERNMENT SUPPORT

This invention was made with United States Government support under National Institutes of Health Grant R37 AI 346776. The United States Government may have certain rights in the invention.

FIELD OF THE INVENTION

The present invention relates to D-amino acid peptides and to pharmaceutical compositions comprising these peptides that are useful for the identification, monitoring and treatment of autoimmune diseases such as systemic lupus erythematosus (SLE) in humans.

BACKGROUND OF THE INVENTION

Autoimmune diseases are characterized by immune responses that are directed against self antigens. These responses are maintained by the persistent activation of self-reactive T lymphocytes. T lymphocytes are specifically activated upon recognition of foreign and/or self antigens as a complex with self major histocompatibility complex (MHC) gene products on the surface of antigen-presenting cells (APC).

Systemic lupus erythematosus (SLE) is a chronic, inflammatory, often multisystemic autoimmune disease which can be acute or insidious in onset. SLE is marked by a wide variety of abnormalities, including arthritis and arthralagias, nephritis, central nervous system manifestations, pleurisy, pericarditis, leukopenia or thrombocytopenia, and hemolytic anemia. One of the most serious complications of SLE is lupus nephritis. Renal involvement usually occurs early in the course of the illness and is the leading cause of death in SLE patients.

SLE is a challenging syndrome for medical professionals because its causes remain to be elucidated and further because it has heterogeneous clinical manifestations. Currently, no specific treatment aimed towards the prevention or cure of SLE is available. Despite the extensive research on the mechanisms underlying the induction of SLE, the information on the etiology of the disease is still limited. Diagnosis of SLE is made on the basis of a number of clinical symptoms such as the so-called "butterfly rash," an erythematous rash which frequently appears on the cheeks of afflicted individuals, crossing the bridge of the nose and becoming more pronounced upon exposure to sunlight; and arthritis which can affect any joint system. However, diagnosis is difficult to verify without appropriate laboratory tests. In this regard, antibodies directed to double-stranded DNA (dsDNA) are diagnostic of SLE and serum titers have long been known to correlate with disease activity in both humans and mice (see, e.g. Pearson et al., J. Immunol. 126:16 (1981)).

Currently, there is no generalized treatment regimen for SLE, although physicians prescribe often prescribe widely immunosuppressive medications such as glucocorticoids. The choice of treatment regimen is typically determined by the individual patient's symptomatology and health status. Consequently, there is a need for broadly applicable treatment regimens, especially for the nephritic manifestations of SLE.

SUMMARY

The invention disclosed herein has a number of embodiments relating to compositions comprising a D-amino acid peptide having the sequence: FIEWNKLRFRQGLEW and methods for using such compositions in a variety of contexts.

This 15-mer peptide is termed "D-pCons" for D form of pConsensus. As discussed herein, when administered to BWF1 mice with systemic lupus erythematosus, D-pCons induces T cells of several types known to prevent autoantibody production and nephritis when administered prior to disease, and also suppress those features in established disease. Correlatively, humans with SLE have T cells that can be educated in vitro to become regulatory T cells that suppress T cells that help induce disease. In this context, the disclosure provided herein provides evidence that D-pCons compositions can therefore be used to induce tolerance in an individual having SLE that is administered this tolerizing peptide. Moreover, the D form of the peptide are typically more resistant to degradation by acid and proteases and thus particularly well suited to be administered orally, making the peptide well suited for therapeutic administration to humans. In addition, the general principles associated with the disclosed compositions and methods for using them are applicable to other autoantibody-mediated diseases, such as myasthenia gravis, and immune hemolytic anemias and Thrombocytopenias.

The use of L-forms of autoantibody-based peptides have completed a phase II clinical trial in patients with SLE in which the peptide was administered by subcutaneous injection. This L-form peptide designated "Edratide" by Teva Pharmaceuticals has similar effects to the L-form of the pConsensus (L-pCons) peptide. Administration of these L-amino acid peptides to mouse models of SLE induce CD4+ CD25+ regulatory T cells and CD8+ suppressive T cells, all cells capable of transferring protection from disease. In human SLE cells transferred into SCID mice, Edratide suppresses autoantibody production. In human SLE cells cultured with L-pCons in vitro, CD4+ CD25+ Foxp3+ regulatory T cells expand significantly among patients with antinuclear antibodies and/or antibodies to DNA, two antibodies characteristic of SLE. The disclosure provided herein demonstrates the surprising finding that D-pCons will both bind and also induce regulatory CD4+CD25hiFoxp3+ T cells (regulatory T cells) when administered to mammals. Moreover, the D form of the consensus peptide has a structure known to be resistant to degradation by acid and proteases and thus is particularly well suited to be administered orally.

In previous murine studies, L-pCons has been identified as having the ability to both bind T cells and induce a functional response in these bound cells when administered intravenously or subcutaneously. For example, L-pCons prolongs survival of BWF1 mice genetically destined to develop SLE by 4-5 months if started prior to disease onset, and by 3-4 months if started after nephritis and anti-DNA antibodies have appeared. The intravenous (i.v.) administration of L-pCons causes anergy in CD4+ CD25− effector T cells that drive production of anti-DNA antibodies, and induces CD4+ CD25+ Foxp3+ regulatory T cells (that suppress anti-DNA and nephritis), and CD8+ Foxp3+ cells that also suppress anti-DNA and nephritis. A single adoptive transfer of the CD8+ pCons-induced T cells protects recipients from autoimmunity for several weeks. We have also shown the in vitro ability of L-pCons to expand Treg in human T cells from patients with SLE. In one vaccination protocol for example, we show that administration of DNA encoding human Ig containing L-pCons to lupus-prone mice also induces suppressive CD8+ T cells and reduces autoimmunity. As disclosed herein, D-pCons has a number of unexpected properties which mimic those observed for L-pCons.

As disclosed herein, the D-pCons peptide (i.e. a peptide having an architecture controlled by D-amino acids instead of L-amino acids) given i.v. and/or orally is surprisingly recognized by T-cells adapted to recognize L-amino acid polymers as observed for example by the ability of the D-pCons peptide to induce CD8+ suppressive T cells. As discussed in detail below for example, D-pCons given orally or I.V. mimics the effects of L-pCons in vivo including the binding and induction of suppressive CD8+ T cells, T cells that can prevent anti-DNA antibody production. This discovery shows that like L-pCons, D-pCons binds and induces CD4+ CD25+ Foxp3+ regulatory T cells and CD8+ Foxp3+ suppressor T cells, both of which downregulate autoimmune responses. These discoveries in addition to what is known about the relative stability of D-amino acid peptides provides evidence that D-pCons will induce tolerance when given orally. In this context, embodiments of the invention include methods for the oral administration of D-pCons in a manner that induces immune tolerance to self (e.g. by decreasing the production of autoantibodies such as anti-DNA antibodies) with consequent prevention of (or suppression of) associated pathologies such as nephritis.

The invention disclosed herein has a number of embodiments. Embodiments of the invention include for example a composition comprising a peptide having the sequence: FIEWNKLRFRQGLEW, wherein at least one amino acid moiety in the peptide is a D-amino acid. Typically, all amino acid moieties in the peptide are D-amino acids. In certain embodiments, the composition further comprises a pharmaceutically acceptable carrier used in orally administered medications. Optionally, the D-amino acid peptide is coupled to a second compound such as avidin or biotin and/or a polyol such as polyethylene glycol and/or a heterologous amino acid sequence such as keyhole limpet hemocyanin.

Embodiments of the invention also include a method of binding a D-amino acid peptide having the sequence: FIEWNKLRFRQGLEW to a T lymphocyte, the method comprising combining the peptide to an antigen-presenting cell with the appropriate MHC with the T lymphocyte receptors under conditions suitable for a binding interaction to occur and then allowing the peptide/MHC complex to bind the T lymphocyte. Such embodiments use the peptide as probe for example to identify the presence of a T lymphocyte in a biological sample as a CD4+ CD25− helper T lymphocyte. In other embodiments, the binding of the peptide to the T lymphocyte is one of the steps in an assay that screens for the presence or susceptibility of a mammal to an immunological disorder, the assay comprising labeling the peptide with a detectable label, incubating the labelled peptide with the T cells so that the labelled peptide is bound to the T cells; and then observing the amount of peptide bound cells, wherein the extent of the binding of the peptide to the T cells is correlated to the presence or susceptibility to the disorder (e.g. an autoimmune disorder characterized by the production of autoantibodies. As disclosed below, such methods can be performed both in vitro and in vivo.

Another embodiment of the invention is a method of inhibiting/suppressing the production of autoantibodies in a mammal (e.g. those that bind nuclear components such as double stranded DNA), the method comprising administering to the mammal an isolated D-amino acid peptide comprising the sequence: FIEWNKLRFRQGLEW, wherein the isolated peptide binds to Major Histocompatibility Complex polypeptides expressed by T cells in the mammal; and further inhibits the production of autoantibodies that bind double stranded DNA in a mammal. In some embodiments, the mammal suffers from an autoimmune disorder comprising systemic lupus erythematosus (SLE) and/or nephritis. Optionally, the D-amino acid peptide is coupled to a heterologous amino acid sequence, for example a constant region from an immunoglobulin. In certain embodiments of the invention, the D-amino acid peptide is administered orally and can be combined with a pharmaceutically acceptable carrier comprising a composition that inhibits acidic or enzymatic degradation of the peptide. Typically in such embodiments, the administration of the D-amino acid peptide results in an induction of CD4+ CD25+ Foxp3+ T cells or CD8+ Foxp3+ T cells in the mammal. In typical embodiments, the administration of the D-amino acid peptide reduces the number of the mammal's splenic B cells that make antibodies that bind double stranded DNA (and/or the relative levels of such antibodies in circulation) by at least about 10%, 20%, 30%, 40% or 50%. In certain embodiments, the administration of the D-amino acid peptide results in a decrease in the concentration of proteins present in the urine of the mammal by at least about 10%, 20%, 30%, 40% or 50%.

In an additional embodiment, the invention concerns articles of manufacture comprising a container and compositions contained within said container, wherein the composition includes peptides of the present invention. The article of manufacture may further comprise instructions for using the peptides in vitro or in vivo. Illustrative embodiments of the invention include a kit, comprising a container and, within the container, an isolated D-amino acid peptide comprising the sequence: FIEWNKLRFRQGLEW, wherein the peptide is capable of binding a T lymphocyte.

DETAILED DESCRIPTION OF THE INVENTION

Figure 1:
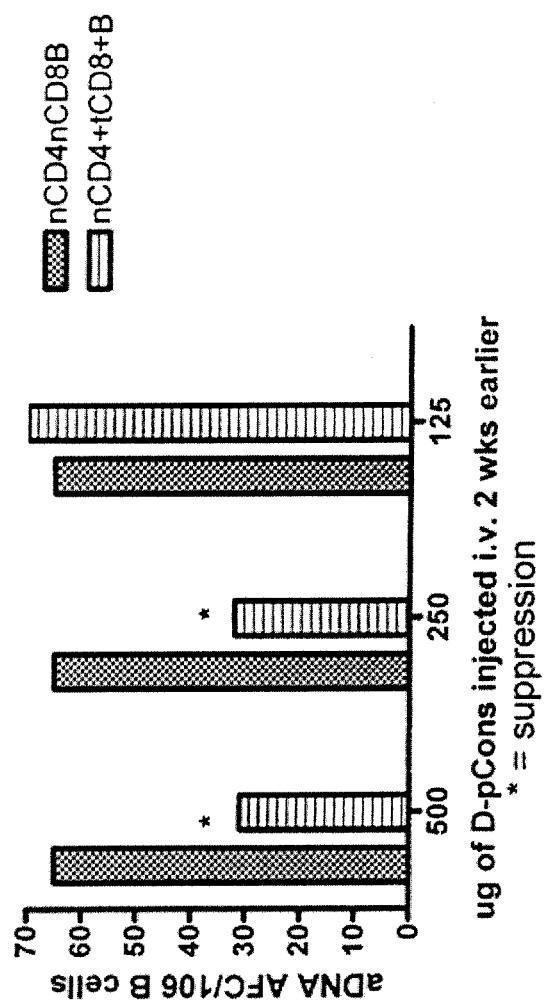
FIG. 1 provides a bar graph of data showing that the intravenous administration of either 500 or 250 ug of D-pCons is effective in suppressing anti-DNA antibody production by naïve BWF1 CD4+ CD25− helper T cells cultured with naïve BWF1 B cells. The numbers of splenic B cells making IgG anti-DNA dropped from 65 per $10^6$ B cells in the untreated group to 30-32 in the tolerized groups.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Ausubel et al., Current Protocols in Molecular Biology, Wiley Interscience Publishers, (1995) and Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

Before the present methods and assays are described, it is to be understood that this invention is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a probe" includes reference to one or more probes and equivalents thereof known to those skilled in the art, and so forth.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

Autoimmune diseases are characterized by immune responses that are directed against self antigens. These responses are maintained by the persistent activation of self-reactive T lymphocytes. T lymphocytes are specifically activated upon recognition of foreign and/or self antigens as a complex with self major histocompatibility complex (MHC) gene products on the surface of antigen-presenting cells (APC).

Systemic lupus erythematosus (SLE) is an autoimmune disease caused primarily by pathogenic autoantibodies (autoAb) and immune complexes containing those autoAb. Although it is normal to make autoAb, individuals predisposed to SLE make higher quantities than healthy individuals and their autoAb repertoire contains Ig that can be pathogenic, i.e. attach to tissue either directly or in immune complexes. Our laboratory has proven that normal mice made transgenic for IgG H and L chains of a murine autoAb directly against DNA is sufficient to cause clinical glomerulonephritis (see, e.g. Tsao et al., J Immunol 1992; 149:350-8).

Autoantibodies arise years before the first clinical symptom of disease in most individuals who later develop SLE (see, e.g. Arbuckle et al., N Engl J Med 2003; 3349:1526-33). Many experts have suggested that a major cause of SLE is loss of ability to regulate quantities and quality of those autoAb.

It was our idea to induce immune tolerance to a family of autoAb represented by pathogenic monoclonal antibodies to DNA. In early work, we were able to induce immune tolerance by i.v. administration of high doses of wild Ig peptides derived from the variable (V) regions of the heavy (H) chains of NZB/NZW F1 (BWFa) murine IgG from monoclonal anti-DNA (see, e.g. Singh et al., J Clin Invest 1995; 96:2990-6).

BWF1 mice spontaneously develop SLE-like disease, worse in females than in males; females die by 50 weeks of age from lupus-like nephritis with renal failure. However, tolerance with wild IgG peptides showed little impact on survival of BWF1 mice. Therefore, we constructed an artificial peptide (L form of pConsensus—referred to as L-pCons) which contains both MHC Class I—(to activateCD8+ T cells) and MHC Class II-binding amino acid sequences known to activate T cells.

Figure 2:
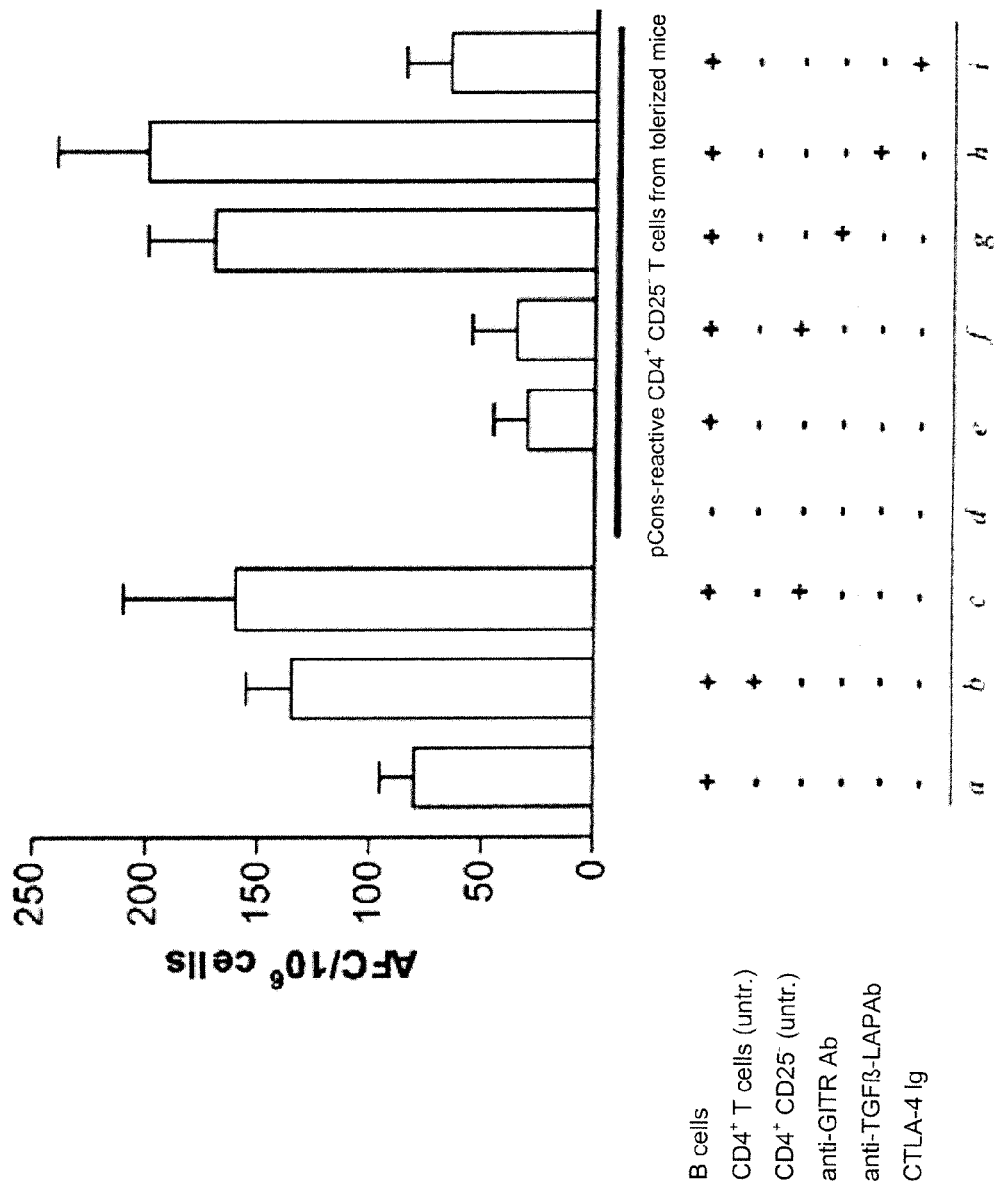
FIG. 2 provides a bar graph of data from studies of L-pCons and D-pCons. Both D-pCons and L-pCons peptides were given once i.v. and spleen cells harvested 2 weeks later. Note that for L-pCons, the combination of naïve B cells plus CD4+ CD25− helper T cells gave a mean of 160 anti-DNA antibody-forming cells per $10^6$ B cells (column 3), whereas addition of CD4+ CD25+ Treg from tolerized mice to the culture reduced the AFC to 25 per $10^6$ B cells (column 4). These differences were statistically significant, $p<0.001$. Note also that the suppression was abrogated by incubation of the cultures with antibodies to GITR (column 6) or TGFb-LAP (column 7), but not by CTLA4-Ig (column 8).
Figure 3:
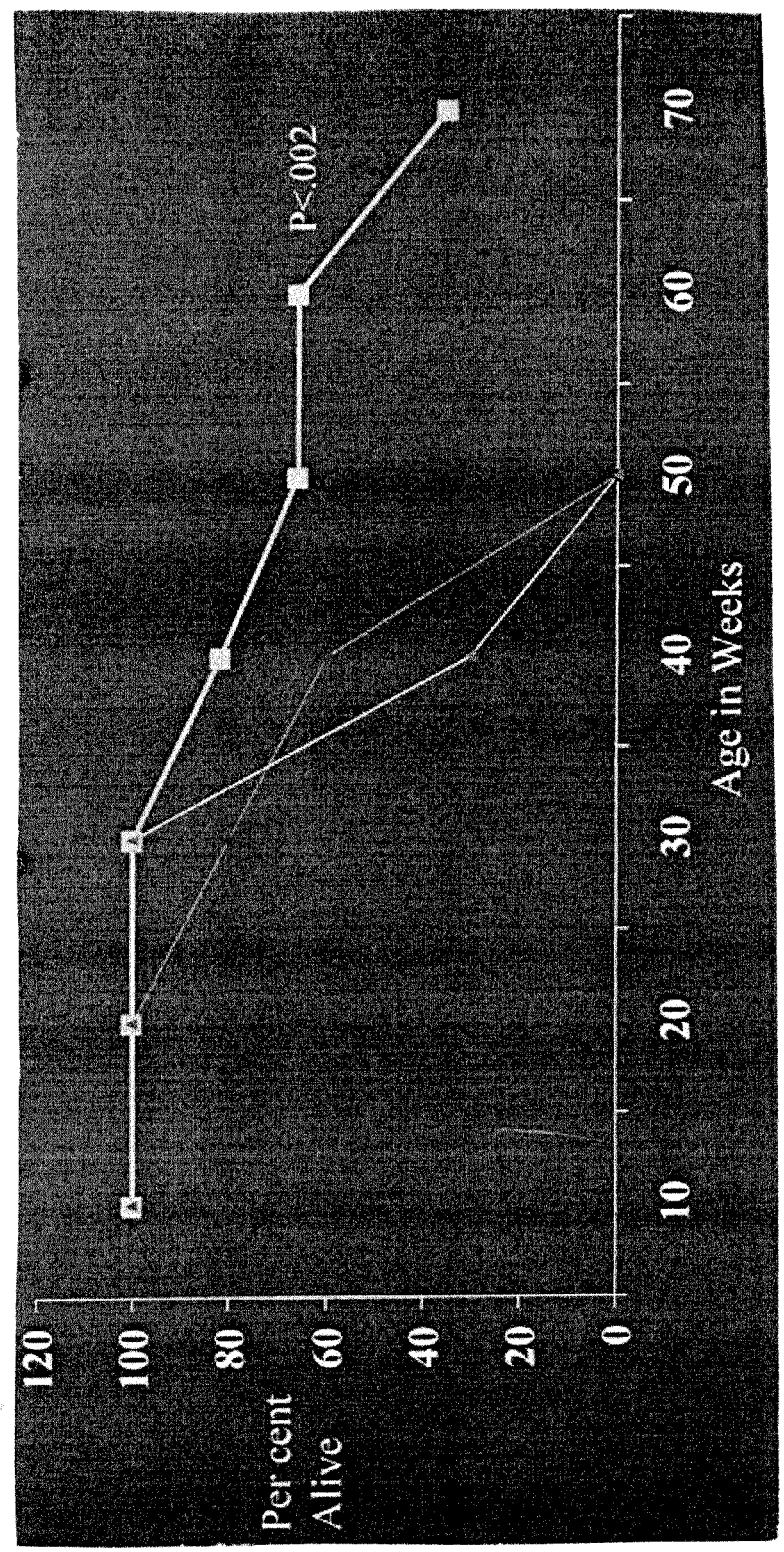
FIG. 3 provides a graph of data showing the suppression of clinical disease that occurs in BWF1 mice treated monthly from age 10 weeks with 1 mg of L-pCons administered intravenously.

Intravenous administration of L-pCons to young BWF1 mice delayed autoAb appearance and nephritis, and prolonged life by several months (see, e.g. Hahn et al., Arthritis Rheum 2001; 44:432-41 and FIG. 3). The mechanism of this effect includes induction of anergy in CD4+ CD25− helper T cells, and induction of both CD4+ CD25+ Foxp3+ regulatory T cells (Treg), and CD8+ Foxp3+ suppressive T cells (Ti), both of which downregulate autoimmunity in BWF1 mice. See, e.g. La Cava et al., J Immunol 2004; 173:3542-8; Hahn et al., Ann NY Acad Sci 2005; 1051:433-41; Hahn et al., J Immunol 2005; 175:7728-37; and Singh et al., J Immunol 2007; 178:7649-57 and FIGS. 2, 4 and 5. We subsequently showed that these Treg and Ti differ from natural innate immunity Treg and CD8+ cytotoxic T cells. They require the tolerizing peptide for activation, whereas natural T cells are not antigen-specific. In addition, the Treg express Foxp3 and work primarily by cell-cell contact, suppressing helper T cell proliferation via membrane-bound TGFb and GITR (see, e.g. La Cava et al., J Immunol 2004; 173:3542-8). Ti also express Foxp3 and suppress CD4+ CD25− helper T cells and B cells primarily by secretion of TGFb (see, e.g. Hahn et al., Ann NY Acad Sci 2005; 1051:433-41; Hahn et al., J Immunol 2005; 175:7728-37; Singh et al., J Immunol 2007; 178:7649-57). More recently, we demonstrated that vaccinating BWF1 mice with DNA encoding pCons induced CD8+ T cells that were capable of suppressing disease (see, e.g. Ferrera et al., Ann NY Acad Sci 2007; 1110:99-111).

Similar observations have been made with related wild peptides from CDR1 and CDR3 of the VH region of other IgG murine antibodies to DNA by Mozes and her colleagues (see, e.g. Eilat et al., J Clin Immunol 2000; 20:268-78; Zinger et al., Int Immunol 2003; 15:205-14; Mauermann et al., Clin Exp Immunol 2004; 137:513-20; Sharabi et al., Proc Natl Acad Sci USA 2006; 103:8810-5; Sela et al., Eur J Immunol 2006; 36:2971-81). In fact, one of the wild peptides they identified, "Edratide", administered by subcutaneous injection, was used in a clinical Phase II trial conducted in human SLE.

In the mouse experiments reported to date, and in the human clinical trials, Ig-related peptides are administered either intravenously (mouse) or subcutaneously (human and mouse). The methods and materials disclosed herein described can be used in studies to 1) improve immune tolerance by inducing not only the Treg and Ti described above, but also by inducing IL-10 and TGFb-secreting T cells derived from the gut-associated lymphoid system by oral tolerance, and 2) improving the practical utility of a therapeutic by administering it orally instead of by i.v. or subcutaneous routes. To this end, we have designed and synthesized the D-form of pConsensus. This enantiomeric molecule has a number of specific advantages over the use of L-pCons. For example, in general, D forms of small peptides resist degradation by gastrointestinal acid and proteases, are absorbed from the GI tract, and persist for several hours in circulation. Therefore this unique chemical compound should provide ample time for induction of peripheral tolerance, and thus for control of SLE.

As shown in the Examples below, a D-enantiomer peptide having the sequence FIEWNKLRFRQGLEW is able to bind MHC class I and Class II polypeptides expressed on the surface of T cells in vivo. As also disclosed herein, this D-enantiomer peptide exhibits additional surprising activities, including for example biological activity including an ability to modulate T cell mediated immune functions (e.g. to reduce the number of the mammal's splenic B cells that make autoantibodies such as those that bind double stranded DNA). Specifically, disclosure presented for example in the Examples below shows that the D-amino acid peptide having the sequence FIEWNKLRFRQGLEW exhibits an architecture that allows it to be bound in vivo by major histocompatibility complex proteins on cells that are evolutionarily adapted to recognize polymers made up of L-amino acid subunits. This is surprising because: (1) the properties of chemical compounds are generally unpredictable in vivo; and (2) with respect to stereoisomers in particular, it is well known that different enantiomers of the same chiral compound can have very different biological properties.

The discovery that the disclosed D-amino acid peptide enantiomer binds major histocompatibility complex proteins is especially unexpected in view of art that teaches that MHC class I and II peptide binding interactions are dependent upon the chirality of the peptide. Specifically, the finding that the D-amino acid peptide having the sequence FIEWNKLR-FRQGLEW exhibits an architecture that allows it to function in vivo by binding the major histocompatibility complex proteins (class I and II) on T cells is particularly surprising in view of art that teaches that D-amino acids play different roles in immune phenomena and further that cross reaction between L- and D-sequences is limited at the T cell level, probably due to different sterical conformations of the MHC-antigen-T cell receptor complexes formed (see, e.g. Sela et al., FASEB J. 11, 449-456 (1997)). Such prior art studies show for example that less than half of a population of T cell hybridomas that are specific for a given L-enantiomer peptide can respond to the corresponding D-enantiomer. Consequently artisans cannot use the MHC class I or II binding activity of a L-amino acid peptide to reasonably predict the binding activity of a corresponding D-amino acid peptide, much less any functional activity that may result from such binding. While the reason for this discouraging lack of predictability is unclear, without being bound by a specific scientific theory, observations that L-amino and D-amino acid peptides exhibit differential hydration properties as well as structure and transition energies suggest that this phenomena may be governed by these differential material properties of the D and L enantiomers exerting dissimilar effects on the sensitive affinity and avidity coefficients that govern the equilibrium association and dissociation constants of the MHC Class I and Class II protein/peptide binding interactions (see, e.g. Scolnik et al., Phys Chem Phys 2006; 8(3): 333-9; and Berezhkovskiy et al., 2002; 308(2): 239-246).

ILLUSTRATIVE EMBODIMENTS OF THE INVENTION

Embodiments of the invention related to peptides comprising D-amino acid residues and methods for making an using such peptides. In particular, every amino acid (except glycine) can occur in two isomeric forms, because of the possibility of forming two different enantiomers (stereoisomers) around the central carbon atom. By convention, these are called L- and D-forms, analogous to left-handed and right-handed configurations. L-amino acids are manufactured in cells and incorporated into proteins. Some D-amino acids are found in the cell walls of bacteria, but not in bacterial proteins. Glycine, the simplest amino acid, has no enantiomers because it has two hydrogen atoms attached to the central carbon atom. Only when all four attachments are different can enantiomers occur.

The invention disclosed herein has a number of embodiments. One is a composition comprising an isolated peptide having the sequence: FIEWNKLRFRQGLEW, wherein at least one amino acid moiety in the peptide is a D-amino acid. Typical embodiments of the invention include compositions comprising a peptide having the sequence FIEWNKLRFRQGLEW, wherein 14 of the 15 amino acids in this composition are D-amino acid moieties. In this context, as is known in the art, the D-form amino acids can be incorporated at any position in the peptide as desired. Thus, for example, in one embodiment, the peptide can comprise a single D-amino acid, while in other embodiments, the peptide comprises at least two, at least three, more at least four, or 5, 6, 7, 8, 9, 10, 11, 12, 13, or 14 D amino acids. In some embodiments, essentially every other amino acid is a D-form amino acid. In certain embodiments at least 90%-95% of the amino acids are D-form amino acids.

Because the data disclosed herein shows that, like the L-enantiomer peptide, a peptide having sequence FIEWNKLRFRQGLEW wherein 14 of 15 amino acids in this composition are D-amino acid moieties can also bind T cells and modulate their activity, it is expected that those peptides that have L-amino residues in combination to D-amino acid residues (and are therefore stereochemically more similar to the L-enantiomer) will exhibit a similar activity. As is known in the art, D-amino acids are incorporated at one or more positions in the peptide simply by using a D-form derivatized amino acid residue in the chemical synthesis. D-form residues for solid phase peptide synthesis are commercially available from a number of suppliers (see, e.g., Advanced Chem Tech, Louisville; Nova Biochem, San Diego; Sigma, St Louis; Bachem California Inc., Torrance, etc.). Those of skill in the art understand that embodiments of the invention include the D-amino acid peptide (i.e. a peptide having at least one D-amino acid moiety) as well as the salts of this peptide (e.g. pharmaceutically acceptable salts known in the art). For example, as is known in the art, peptides can occur both as a free acid form as well as peptide sodium, potassium or ammonium salts, and other salts derived from alkaline earth elements or other metallic salts.

A similar embodiment of the invention is D-amino acid peptide selected from the group consisting of a peptide of at least 14 D-amino acid residues having the sequence FIEWNKLRFRQGLEW and/or a salt thereof and/or the reaction product thereof with an organic derivatizing agent capable of reacting with selected side chains or terminal residues, which reaction product retains at least a portion of the function of the peptide to inhibit specifically the proliferative response and cytokine secretion of T lymphocytes of mice that are high responders to SLE-inducing autoantibodies and/or a chimeric peptide comprising the sequence FIEWNKLRFRQGLEW linked to a heterologous amino acid sequence.

In certain embodiments, the D-amino acid peptide is coupled to a second molecule. For example, the FIEWNKLRFRQGLEW peptide of the present invention can be modified to form a chimeric molecule comprising FIEWNKLRFRQGLEW conjugated to another molecule such as a polyol (e.g. polyethylene glycol), a small molecule such as avidin or biotin, or heterologous polypeptide or amino acid sequence such as the keyhole limpet hemocyanin protein. A variety of methods for conjugating such molecules are known in the art including for example those disclosed in U.S. Patent Application Nos. 20070111926 and 200501649523.

A chimeric molecule can comprise a fusion of FIEWNKLRFRQGLEW for example with a polyhistidine epitope tag or the like, which provides a further epitope for manipulation (e.g. an epitope to which immobilized nickel can selectively bind). A variety of such epitope tags are well known in the art and are generally placed at the amino- or carboxyl-terminus of peptides. In an alternative embodiment, the chimeric molecule can comprise a fusion of FIEWNKLRFRQGLEW with a polypeptide known to facilitate stability such as an immunoglobulin polypeptide sequence or a particular region of an immunoglobulin or the like. Such a fusion can be for example to the Fc region of an IgG molecule. The Ig fusions can include a substitution of an Ig region or domain or part thereof substituted with FIEWNKLRFRQGLEW. In one such embodiment, the immunoglobulin fusion can include the hinge and/or CH2 and/or CH3 regions, or the hinge, CH1, CH2 and/or CH3 regions of an IgGI molecule. Descriptions of methods for making and using such molecules are disclosed for example in Jones et al., Nature 321:522-525 (1986); Riechmann et al., Nature 332:323-329 (1988); Presta, Curr. Op. Struct. Biol. 2:593-596 (1992); U.S. Pat. No. 5,428,130 issued Jun. 27, 1995 and Chamow et al., TIBTECH, 14:52-60 (1996).

Another embodiment of the invention is a method of selecting chimeric peptides capable of inhibiting the proliferative response of T lymphocytes from a systemic lupus erythematosus (SLE) patient, comprising: (i) a peptide of at least 14 of 15 D-amino acid residues having the sequence FIEWNKLRFRQGLEW; (ii) coupling this peptide to a heterologous amino acid sequence to form a chimeric peptide; and (iii) testing said chimeric peptide for its ability to inhibit the proliferative response of T cells from a SLE patient, or an SLE associated T cell line or clone; and (iv) selecting and producing additional quantities of said chimeric peptide only if it is capable of inhibiting said proliferative response.

In certain embodiments, the peptides of the invention are combined with a pharmacologically acceptable excipient (e.g. an excipient suitable for oral administration to a mammal). An example of this is a D-amino peptide having the sequence FIEWNKLRFRQGLEW further comprising a pharmaceutically acceptable carrier used in orally administered medications. Another example of this is a D-amino peptide having the sequence FIEWNKLRFRQGLEW, further comprising a pharmaceutically acceptable carrier used in parenterally administered medications.

As noted above, the peptides of this invention (e.g. D-amino peptide having the sequence FIEWNKLRFRQGLEW and/or this peptide coupled to a heterologous amino acid sequence to form a chimeric peptide) are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). For example, therapeutic compositions comprising an embodiment of the invention can be prepared by mixing the desired peptide having the appropriate degree of purity with pharmaceutically acceptable carriers, excipients, or stabilizers in the form of lyophilized formulations, aqueous solutions or aqueous suspensions (see, e.g. Remington: The Science and Practice of Pharmacy Lippincott Williams & Wilkins; 21 edition (2005), and Ansel's Pharmaceutical Dosage Forms and Drug Delivery Systems Lippincott Williams & Wilkins; 8th edition (2004)).

Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers. The peptide is preferably admixed with a carrier comprising a buffering agent and one or several agents selected from the group consisting of carbohydrates and modified carbohydrates and derivatives thereof, polyethylene and/or polypropylene glycol and derivatives thereof, organic and inorganic core, filler or lubricating materials, fatty acids, their esters and salts, preservatives, antioxidants, and coating agents. The buffering agent should be able to buffer at a pH from about 3 to about 6, preferably at about pH 5.5, i.e. to exert substantial buffer capacity within this range and preferably at about pH 5.5. Since the composition according to the invention is intended for preferred release in the upper part of the small intestine where, during their passage, the acidic contents of the stomach are neutralized by influx of Na+, buffering inhibits or delays an increase of pH exceeding the preferred range or, in other words, in the direction of the upper limit of the preferred range and exceeding its upper limit. Preferred buffering agents are hydrogen and dihydrogen phosphates, such as sodium dihydrogen phosphate and mixtures of sodium dihydrogen phosphate with disodium hydrogen phosphate, calcium tetrahydrogen phosphate, citric acid and mixtures of citric acid and its monosodium salt, fumaric acid and its monosodium salt, adipic acid and its monosodium salt, tartaric acid and its sodium salt, ascorbic acid and its monosodium salt, glutamic acid, aspartic acid, betaine hydrochloride, hydrochlorides of amino acids, such as arginine monohydrochloride and glutamic acid hydrochloride, and saccharic acid. It is preferred for the buffering agent to comprise at least 10% by weight, more preferred at least 25% by weight, most preferred at least 40% by weight of the composition according to the invention. A mixture of two or more buffering constituents can be used.

Unlike typical peptide formulations, the peptides of this invention comprising D-form amino acids can be administered, even orally, without protection against proteolysis by stomach acid, etc. Nevertheless, in certain embodiments, peptide delivery can be enhanced by the use of protective excipients. This is typically accomplished either by complexing the polypeptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid compositions for oral delivery of therapeutic agents).

The compositions of the invention are useful in a variety of diagnostic and therapeutic contexts. In certain embodiments of the invention, the peptide can be coupled to a detectable marker and used as a probe, for example to identify T cells in a biological sample (e.g. a biopsy sample) and in particular, a Treg or Ti cell. In other embodiments, the peptide is used as a diagnostic tool to obtain evidence on the presence or susceptibility that a mammal may have for an immunological disorder such as SLE. For example, one embodiment of the invention is an assay for screening the presence of or susceptibility to a mammal to an immunological disorder, comprising labeling a D-amino acid peptide composition comprising the sequence FIEWNKLRFRQGLEW with a detectable label, wherein the peptide comprises a T-cell epitope having a sequence corresponding to a stretch of the sequence of the antigen relevant to the disorder and binds to gene products of the major histocompatibility complex (MHC), classes I and II, on the surface of intact living antigen presenting cells; incubating intact living antigen-presenting cells with the labelled peptide, thus directly binding the peptide to the cells; and then monitoring the extent of binding by the addition of a probe that reacts with the ligand and measuring peptide bound cells versus peptide-unbound cells, whereby the extent of the binding of the peptide to the antigen-presenting cells is correlated to the presence of and/or susceptibility to the disorder. Suitable labels in this context include, but are not limited to, a radioisotope, a fluorescent compound, a bioluminescent compound, chemiluminescent compound, a metal chelator or an enzyme. Optionally in such assays, the disorder screened for is systemic lupus erythematosus.

Embodiments of the invention further relate to therapeutic agents that will interfere with the binding to MHC gene products and thus, inhibit T-cell responses that are relevant to the disease. For example, in one embodiment, this invention provides methods for ameliorating and/or preventing one or more symptoms of SLE. The methods preferably involve administering to an organism, preferably a mammal, more preferably a human one or more of the peptides of this invention. The peptide(s) can be administered, as described herein, according to any of a number of standard methods including, but not limited to injection, suppository, nasal spray, time-release implant, transdermal patch, and the like. In one particularly preferred embodiment, the peptide(s) are administered orally (e.g. as a syrup, capsule, or tablet).

Embodiments of the invention also include a method of binding a D-amino acid peptide having the sequence: FIEWNKLRFRQGLEW to a T lymphocyte, the method comprising combining the peptide with the T lymphocyte under conditions suitable for a binding interaction to occur and then allowing the peptide to bind the T lymphocyte. Such embodiments can use the peptide as probe for example to identify the presence of a T lymphocyte in a biological sample as a CD4+ CD25− helper T lymphocyte. In other embodiments, the binding of the peptide to the T lymphocyte comprises an assay for screening the presence or susceptibility of a mammal to an immunological disorder, the assay comprising labeling the peptide with a detectable label, incubating the labelled peptide with the T cells so that the labelled peptide is bound to the T cells; and then observing the amount of peptide bound cells, wherein the extent of the binding of the peptide to the T cells is correlated to the presence or susceptibility to the disorder (e.g. an autoimmune disorder characterized by the production of autoantibodies. As disclosed below, such methods can be performed both in vitro and in vivo. In certain in vivo embodiments, the binding of the peptide to the T lymphocyte comprises a therapeutic method designed to treat an immune disorder such as SLE Another embodiment of the invention is a method of inhibiting the production of autoantibodies that bind double stranded DNA in a mammal, the method comprising administering to the mammal an isolated D-amino acid peptide comprising the sequence: FIEWNKLRFRQGLEW, wherein the isolated peptide binds to Major Histocompatibility Complex polypeptides expressed by T cells in the mammal; and further inhibits the production of autoantibodies that bind double stranded DNA in a mammal. In some embodiments, the mammal suffers from an autoimmune disorder comprising systemic lupus erythematosus (SLE) and/or nephritis. Optionally, the D-amino acid peptide is coupled to a heterologous amino acid sequence, for example a constant region from an immunoglobulin. In certain embodiments of the invention, the D-amino acid peptide is administered orally and can be combined with a pharmaceutically acceptable carrier comprising a composition that inhibits acidic or enzymatic degradation of the peptide. Typically in such embodiments, the administration of the D-amino acid peptide results in an induction of CD4+ CD25+ Foxp3+ T cells or CD8+ Foxp3+ T cells in the mammal. In typical embodiments, the administration of the D-amino acid peptide reduces the number of the mammal's splenic B cells that make antibodies that bind double stranded DNA by at least about 50%. In certain embodiments, the administration of the D-amino acid peptide results in a decrease in the concentration of proteins present in the urine of the mammal.

A related embodiment of the invention is a method of treating an animal having systemic lupus erythematosus (SLE) and a SLE-associated manifestation of nephritis, autoantibodies, and inflammation associated with autoantibodies, said method comprising administering to said animal a therapeutically effective amount of an isolated D-amino acid peptide comprising the sequence: FIEWNKLRFRQ-GLEW, wherein said isolated peptide is capable of specifically binding with a T cell receptor present on a T cell in an animal having SLE, and/or is capable of promoting immunological tolerance in an animal, thereby treating said SLE and said SLE-associated manifestation. Methods and materials that can be used and/or adapted for such methods are described for example in U.S. Patent Application No. 20070003543.

Another embodiment of the invention is a method of treating a subject having glomerulonephritis, the method comprising administering to said subject at least one peptide that binds to an anti-double stranded-DNA antibody in the subject, wherein: said peptide comprises a D-amino acid sequence: FIEWNKLRFRQGLEW; and an amount of peptide administered is effective to treat at least one sign or symptom of glomerulonephritis. Optionally these methods further comprise the step of selecting the subject as an individual diagnosed with systemic lupus erythematosus.

In the therapeutic embodiments of the invention, the peptides of the invention are administered in a therapeutically effective amount. The term "therapeutically effective amount" refers to an amount of an agent (e.g. a peptide comprising a D-amino acid sequence: FIEWNKLRFRQ-GLEW) effective to treat at least one sign or symptom of a disease or disorder in a human (e.g. SLE). Amounts of an agent for administration may vary based upon the desired activity, the diseased state of the patient being treated, the dosage form, method of administration, patient factors such as the patient's sex, weight and age, the underlying causes of the condition or disease to be treated, the route of administration and bioavailability, the persistence of the administered agent in the body, the formulation, and the potency of the agent. It is recognized that a therapeutically effective amount is provided in a broad range of concentrations. Such range can be determined based on in vitro and/or in vivo assays.

Effective dosages and schedules for administering the D-amino acid peptides of the invention may be determined empirically, and making such determinations is within the skill in the art. Those skilled in the art will understand that the dosage of D-amino acid peptide that must be administered will vary depending on, for example, the mammal which will receive the peptide, the route of administration, the particular type of peptide used and other drugs being administered to the mammal. Guidance in selecting appropriate doses is found in the literature, for example, on therapeutic uses of peptides such as for example: *Therapeutic Peptides and Proteins: Formulation, Processing, and Delivery Systems*, Second Edition by Ajay K. Banga (2005); *Pharmaceutical Dosage Forms: Parenteral Medications*, Volume I (Parenteral Medications, 1) by Kenneth E. Avis, Herbert A. Lieberman, and Leon Lachman (1992); and *Goodman & Gilman's The Pharmacological Basis of Therapeutics* by Laurence Brunton, John Lazo, and Keith Parker (2005). A typical daily dosage of D-amino acid peptide used alone might range from about 0.5 mg/kg to 1, 5, 10, 20, 30, 40, 50, 60, 70, 80, 90 and up to 100 mg/kg of body weight or more per day, depending on the factors disclosed herein (see, e.g. mouse dose data in Example 2).

EXAMPLES

Example 1

Illustrative Methods and Materials Associated with Embodiments of the Invention

Mice

NZB ($H-2^{d/d}$), NZW ($H-2^{z/z}$), Balb/c and (NZB×NZW) F1 ($H-2^{d/z}$) mice were bred and maintained at the University of California Los Angeles (UCLA) or purchased from The Jackson Laboratories (Bar Harbor, Me.). All mice were housed in pathogen free conditions and were treated in accordance with the guidelines of the University of California Los Angeles Animal Research Committee, an Institution accredited by the Association for Assessment and Accreditation of Laboratory Animal Care (AAALAC). All experiments were conducted in female mice.

Peptides

The peptides used in this study and the MHC molecules they bind are described in detail (see, e.g. Singh et al., J Immunol 2007; 178:7649-57). The tolerizing D-amino acid peptide pCons (FIEWNKLRFRQGLEW (SEQ ID NO: 1)) is artificial; it contains T cell determinants based on the J558 $V_H$ regions of several murine mAb anti-dsDNA from BWF1 mice. The negative control peptide pNeg (AIAWAKARAR-QGLEW) (SEQ ID NO: 3) binds I-Ed (expressed by BWF1) but is non-stimulatory and non-tolerogenic. Wild 12-mer or 15-mer peptides from $V_H$ of BWF1 anti-DNA Ab that stimulate CD4'T cells from BWF1 mice include p7 (GYFMN-WVKQSHGKSL) (SEQ ID NO: 4), p34 (MNWVKQSH-GKSL) (SEQ ID NO: 5) and p58 (FYNQKFKGKATL) (SEQ ID NO: 6) (see, e.g. Singh et al., J Immunol 2007; 178:7649-57). PCDR1 (TGYYMQWVKQSPEKSLEWIG) (SEQ ID NO: 7) is a wild stimulatory peptide described by Eilat et al (see, e.g. Eilat et al., J Clin Immunol 2000; 20:268-78) from a similar region in the $V_H$ of a murine mAb anti-DNA Ig. Other non-stimulatory control peptides are pHyHEL (VKQRPGHGLEWIGEI) (SEQ ID NO: 8), derived from the $CDR_1/Fr_2$ $V_H$ region of a murine Ab against hen egg lysozyme (HEL), and p11 and p93, which derive from the same $V_H$ of the stimulatory wild Ig peptides as p7, p34 and p58 (BWF1 anti-DNA Ab A6.1). Peptides were synthesized at Chiron Biochemicals (San Diego, Calif.), purified to single peak on high-performance liquid chromatography, and analyzed by mass spectroscopy for expected amino acid content.

Treatment of Mice

For tolerance induction, ten-to-twelve week-old BWF1 mice received a single i.v. dose of 1 mg of one of the peptides, dissolved in saline, as reported previously (see, e.g. Singh et al., J Clin Invest 1995; 96:2990-6). Controls in selected experiments were either treated with saline or control peptides.

Cell Isolation and Staining

Spleen cells were isolated from saline-treated, naïve or tolerized, BWF1 mice one-week after administration of pCons after lysis of red blood cells with ACK lysing buffer (Sigma, St. Louis, Mo.). Cell subsets were purified by incubation with anti-CD4, anti-B and anti-CD8+, anti NK1.1, anti Mac-3, anti Gr-1, microbeads from (Miltenyi Biotech, Auburn, Calif.). A total of 1×2×10⁶ freshly isolated spleen cells or CD8⁺ T cells were used for staining of cell surface molecules. Antibodies used to analyze the cells included anti-Thy1.2, Anti-CD4, Anti-B220, anti-CD8, anti-CD25 and anti-CD28 (all from BD Pharmingen, San Diego, Calif.).

Cell Sorting

Cell sorting was performed on stained splenocytes from naïve and pCons treated mice. Splenocytes were prepared after RBC lysing and 10×10⁶ cells/ml were stained with FITC conjugated anti-mouse CD8, APC conjugated CD28 Abs from BD Pharmingen, San Diego, Calif. Cells were sorted with FACS SE Vantage (Becton Dickinson) at the UCLA Flow cytometry Core facility.

Immunophenotyping

Isolated cells were washed with FACS buffer and 1-2 million cells were used for surface staining and immunophenotyping. Before staining, cells were incubated with rat anti-mouse CD16/CD32 (FCγ III/II receptor) monoclonal antibody to block-nonspecific binding. Cells were then stained with Abs to anti-mouse CD3 (clone-145-2C11), CD8a (Ly-2) (53-6.7), CD4 (L3T4), (clone-RM4-5), CD45R/B220 (RA3-6B2), NK1.1 (PK136), CD49b/Pan NK (Dx5), Mac-3 (M3/84), GR-1 (RB6-8C5), CDIIc (HL-3), CD25 (PC61), CD28 (37.51), CD44 (IM7), CD56 (MEM-188), CD62L (MEL-14), CD122 (TM-β1), CD137-41BB (IAH2), Granzyme B (16G6), Perforin (e BioOMAK-D) and CTLA-4 (UC10-4F10-11). Immunophenotyping of splenocytes from untreated and pCons-tolerized mice was performed with a FACSCalibur™ flow cytometer (BD Biosciences, San Jose, Calif.) using either Cell Quest (BD Biosciences) or FCS Express software (De Novo Software, Thorn hill, ON). Forward and side-scatter parameters were used to gate on live cells. Staining with multiple combinations of Ab was performed according to standard procedures described elsewhere (see, e.g. La Cava et al., J Immunol 2004; 173:3542-8; Hahn et al., Ann NY Acad Sci 2005; 1051:433-41). Staining with annexin V and with −7AAD was used to distinguish cells undergoing apoptosis from necrotic dead cells. The conjugated Abs used were purchased from BD Pharmingen and e Biosciences (San Diego, Calif.).

In Vitro Suppressive Assay

Spleen cells were isolated from BWF1 mice after one-week of pCons treatment as described before. B220⁺ B cells, CD4⁺, and CD8⁺T cells were isolated via magnetic bead separation using Vario Macs apparatus (Miltenyi Biotech). CD4⁺ T cells, CD4⁺ CD25⁻ cells, as responders, irradiated and non-irradiated B cells as antigen presenting cells, and CD8⁺ T cells as suppressors from pCons treated mice were used in the experiments. 1×10⁵ isolated cells were cultured in triplicate in 96-well plates with varying amounts of CD8⁺ T cells, 2×10⁵ irradiated and non-irradiated B cells with 20 µg/ml of pCons or control peptides to activate suppression for 96 hours, then pulsed with 0.5 µCi/well [³H] thymidine (Perkin Elmer, Wellesley, Mass.) during the last 18 h of culture. Cells were harvested using an automated cell harvester onto filters, and radioactivity was counted in a Beckman scintillation counter.

Intracellular Staining

For Intracellular Staining, Cells were First Stained for Expression of Cell Surface Markers and then Fixed, Permeabilized, and Stained Using the CytoIN Vitro Suppressive Assay Spleen cells were isolated from BWF1 mice after one-week of pCons treatment as described before. B220⁺ B cells, CD4⁺, and CD8⁺ T cells were isolated via magnetic bead separation using Vario Macs apparatus (Miltenyi Biotech). CD4⁺ T cells, CD4⁺ CD25⁻ cells, as responders, irradiated and non-irradiated B cells as antigen presenting cells, and CD8⁺ T cells as suppressors from pCons treated mice were used in the experiments. 1×10⁵ isolated cells were cultured in triplicate in 96-well plates with varying amounts of CD8⁺ T cells, 2×10⁵ irradiated and non-irradiated B cells with 20 µg/ml of pCons or control peptides to activate suppression for 96 hours, then pulsed with 0.5 µCi/well [³H] thymidine (Perkin Elmer, Wellesley, Mass.) during the last 18 h of culture. Cells were harvested using an automated cell harvester onto filters, and radioactivity was counted in a Beckman scintillation counter.

Intracellular Staining

For intracellular staining, cells were first stained for expression of cell surface markers and then fixed, permeabilized, and stained using the Cyto-fix/cytoperm kit (BD Pharmingen, San Diego, Calif.) according to manufacturer's instructions.

Cytokine Measurement

Cytokine measurement in the supernatant of cultured spleen cells was done with BD OptEIA™ ELISA kits (BD Biosciences and Bio legends Inc., San Diego, Calif.) for IFNγ, IL-2, TGFβ and IL-10. Intracellular mRNA encoding IFNγ, IL-10, Foxp3 and TGFβ was analyzed by real-time RT PCR. GAPDH was used as a house-keeping gene for normalization.

Assays for Measurement of Anti-DNA Ab

Assays were performed to measure anti-DNA Ab according to art accepted protocols (see, e.g. Singh et al., J Clin Invest 1995; 96:2990-6; Hahn et al., Arthritis Rheum 2001; 44:432-41; La Cava et al., J Immunol 2004; 173:3542-8; Hahn et al., Ann NY Acad Sci 2005; 1051:433-41; Hahn et al., J Immunol 2005; 175:7728-37; Singh et al., J Immunol 2007; 178:7649-57). For optimal antibody production, we co-cultured B cells from old naïve BWF1 females with 2+ proteinuria or higher, with CD4⁺T cells from young 10-12 week old naïve BWF1 females without proteinuria, and with CD8⁺ T cells from 10-12 week-old females treated one week prior with saline or pCons. Ratios are 1 B cell to 10 CD4⁺ T cells to 10 CD8⁺ T cells. After 5 days, culture supernatants were collected, concentrated, and analyzed for anti-DNA IgG by ELISA.

Real-Time PCR

Real-time PCR was analyzed according to art accepted protocols (see, e.g. Hahn et al., Ann NY Acad Sci 2005; 1051:433-41). Briefly, total RNA was isolated with TRIzol (Invitrogen Life Technologies, Carlsbad, Calif.) as per manufacturer's protocol. Reverse transcription used 50 ng of total RNA. The oligonucleotide sequences used for the primers and TaqMan probes are as follows; IFN-γ forward, 5' TGA GAC AGA AGT TCT GGG CTTCT 3' (SEQ ID NO: 9); reverse, 5' CAAGAT GCA GTG TGT AGC GTTCA 3' (SEQ ID NO: 10): probe, 6FAM TCC TGCGGCCTAGCTCT-GAGA TAMRA (SEQ ID NO: 11). IL-10 forward, 5' CAG CCG GGA AGA CAA TAA CTG 3' (SEQ ID NO: 12); reverse, 5' CCG CAG CTC TAG GAG CAT GT 3' (SEQ ID NO: 13); probe 6FAM ACC CAC TTC CCA GTC GGC CAG AG TAMRA. TGFβ forward, 5' AAACGGAAGCGCATC-GAA 3' (SEQ ID NO: 14); reverse, 5' GGGACTGGCGAGC-CTTAGTT 3' (SEQ ID NO: 15), probe 6FAM CCATC-CGTGGCCAGATCCTGTCC TAMRA (SEQ ID NO: 16). Foxp3 forward, 5'TGCAGGGCAGCTAGGTACTTGTA 3' (SEQ ID NO: 17); reverse, 5' TCTCGGAGATC-CCCTTTGTCT 3' (SEQ ID NO: 18); probe 6FAM TCCGAACAGCATCATCCTTCTTAGCATCC TAMRA (SEQ ID NO: 19). The amplification primers were at 900 nM and the probe at 200 nM. A passive reference dye (ROX) provided an internal standard for normalization of FAM fluorescence, correcting for fluctuations due to volume changes. For relative quantitation, a standard curve was constructed for each primer and probe set, using total RNA. RNA was isolated from spleen cells of 10-13 week-old naïve or tolerized mice. Spleen cells from 2 to 3 mice in each group were pooled for each experimental group. For some experiments, CD4+ and CD8+ cells were isolated by positive selection using micro beads with Miltenyi AutoMACS as described above. A ribosomal RNA control primer and probe set (Applied Biosystems) were used for normalization purposes. The possibility of genomic DNA contamination was excluded by use of no reverse transcriptase controls in combination with ribosomal primers. GAPDH was used as endogenous control in each experimental set. All samples were run in duplicate. Normalization was employed as indicated in the figure legends.

siRNA Transfection

CD8+ CD28+ and CD8+ CD28 T s suppressive cells and CD8' T cells isolated as described above were plated and cultured in 24 well plates for 24 hours in complete medium containing 10% FCS. For transfection, Silencer siRNA Transfection Kit from Ambion (Austin, Tex.) was used. Opti-MEM reduced serum medium (Gibco BRL) was used to dilute the siPORT amine. Validated siRNA of FoxP3 and GAPDH were obtained from Ambion, as well as positive and negative siRNA controls. The negative control siRNA was a scrambled sequence that bears no homology to human, mouse or rat genomes. The transfection agent alone served as another control (siPORT amine). The agent was mixed with siRNA of Foxp3 (50-100 nM) and GAPDH (50-100 nM) or controls in serum free medium and incubated at RT for 30 min. Cells were transfected with siRNA complexes by overlaying siRNA drop-wise onto the cells. After 8-10 hours, medium was removed and fresh medium (1-2 ml) added. Viability was assayed with trypan blue staining. After 48 hours of culture, transfected CD8+ T cells were transferred to cultures of fresh BWF1 CD4+ T cells plus B cells plus pCons for measurement of suppression of anti-DNA Ab production. Some transfected cells were lysed with cell lysing solution (Invitrogen) and RNA isolated for real-time PCR, to validate knock down of the target gene.

Statistical Analyses

Statistical analyses were performed using Prism 4 software (GraphPad, San Diego, Calif.). Parametric testing between two groups was performed by the paired t-test or by Mann Whitney U test. Non-parametric testing among more than two groups was performed by one-way analysis of variance (ANOVA). P values less than 0.05 were considered significant Results:

D-pCONS is Equivalent to L-pCONS in Ability to Induce Suppression of IgG Anti-DNA Production in BWF1 Mice.

As shown in FIG. 1, intravenous administration of either 500 or 250 ug of D-pCons, was effective in suppressing anti-DNA antibody production by naïve BWF1 CD4+ CD25– helper T cells cultured with naïve BWF1 B cells. The numbers of splenic B cells making IgG anti-DNA dropped from 65 per $10^6$ B cells in the untreated group to 30-32 in the tolerized groups. In contrast, the 125 ug-dose of D-pCons was not effective in inducing suppression.

Compare these data with D-pCons to those with L-pCons, shown in FIG. 2. Both D-pCons and L-pCons peptides were given once i.v. and spleen cells harvested 2 weeks later. Note that for L-pCons in FIG. 2, the combination of naïve B cells plus CD4+ CD25– helper T cells gave a mean of 160 anti-DNA antibody-forming cells per $10^6$ B cells (column 3), whereas addition of CD4+ CD25+ Treg from tolerized mice to the culture reduced the AFC to 25 per $10^6$ B cells (column 4). These differences were statistically significant, p<0.001. Note also that the suppression was abrogated by incubation of the cultures with antibodies to GITR (column 6) or TGFb-LAP (column 7), but not by CTLA4-Ig (column 8).

The ability of D-pCons compared to L-pCons to suppress anti-DNA production when the peptide is fed is currently being studied. Mice are gavaged every other day for 5 days out of each month. After the $2^{nd}$ month, spleen cells are harvested 2 weeks after the onset of the 2' round of feeding. Three different doses are being studied, based on survey of the literature for disease-reducing doses of short linear peptides fed to mice that develop EAE, diabetes type I, or collagen II-induced arthritis—all examples of autoimmune diseases. The doses are 25, 100 and 250 ug.

This data as disclosed herein shows that the D-amino acid peptide as disclosed herein surprisingly exhibits an architecture that allows it to be recognized by cells and/or biological molecules that are evolutionarily adapted to recognize polymers made up of L-amino acid subunits.

Effect of D-pCons Feeding on Clinical Disease.

The anticipated results are shown in FIG. 3. These data show the suppression of clinical disease that occurs in BWF1 mice treated monthly from age 10 weeks with 1 mg of L-pCons intravenously. Using 50% mortality times, the lifespan is prolonged 30-32 weeks. Improved survival was accompanied by significant delay in the appearance of IgG anti-DNA in serum and of nephritis (see, e.g. Hahn et al., Arthritis Rheum 2001; 44:432-41). A similar study has been started with D-pCons administered orally; results are anticipated in 30 weeks. Serum is obtained at regular intervals for anti-DNA testing; urine is tested for proteinuria monthly (when 2+ appears mice are tested weekly), and survival is measured daily.

Assessments of various embodiments of the peptides of the invention are made according to art accepted procedures. For example, after the successful induction of regulatory/suppressive T cells with the oral administration of a peptide embodiment, this peptide embodiment can be tested for its ability to generate similar cells from human lymphocytes in vitro.

Identifying the T cells which Regulate SLE-Like Disease

Figure 4:
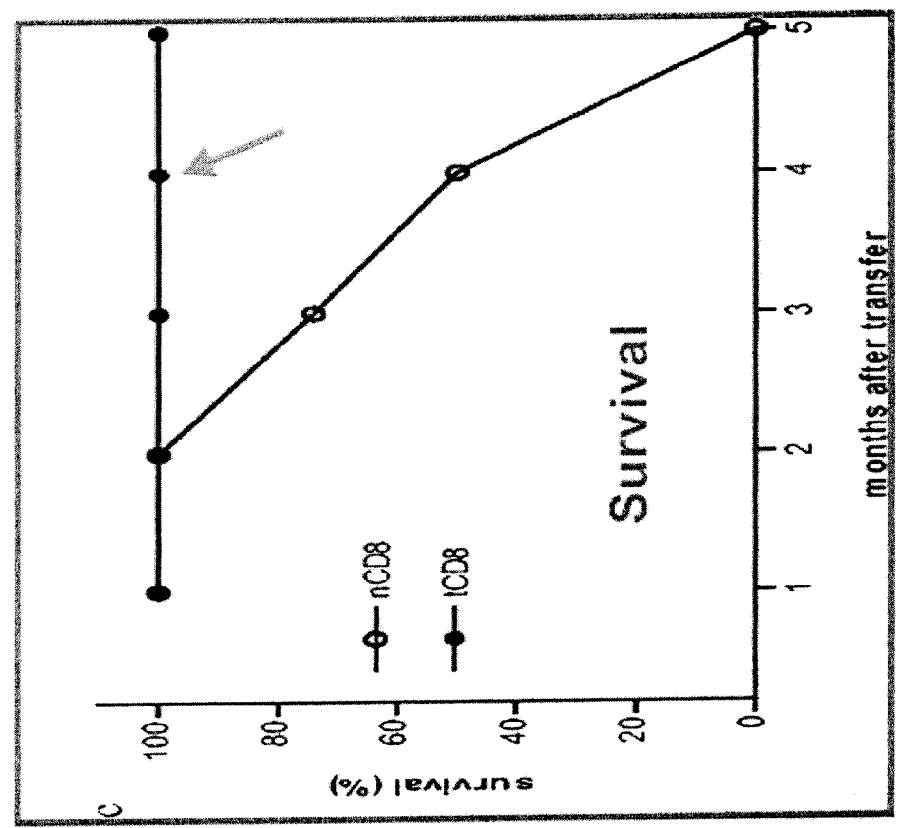
FIG. 4 provides graphs of data showing the CD8+ Ti induced by i.v. administration of L-pCons are potent in suppressing nephritis (left panel) and prolonging survival in vivo (right panel) (see, e.g. Hahn et al., J Immunol 2005; 175: 7728-37). These data represent a single transfer of $10 \times 10^6$ CD8+ T cells from spleens of tolerized mice to sublethally irradiated syngeneic recipients.
Figure 4:
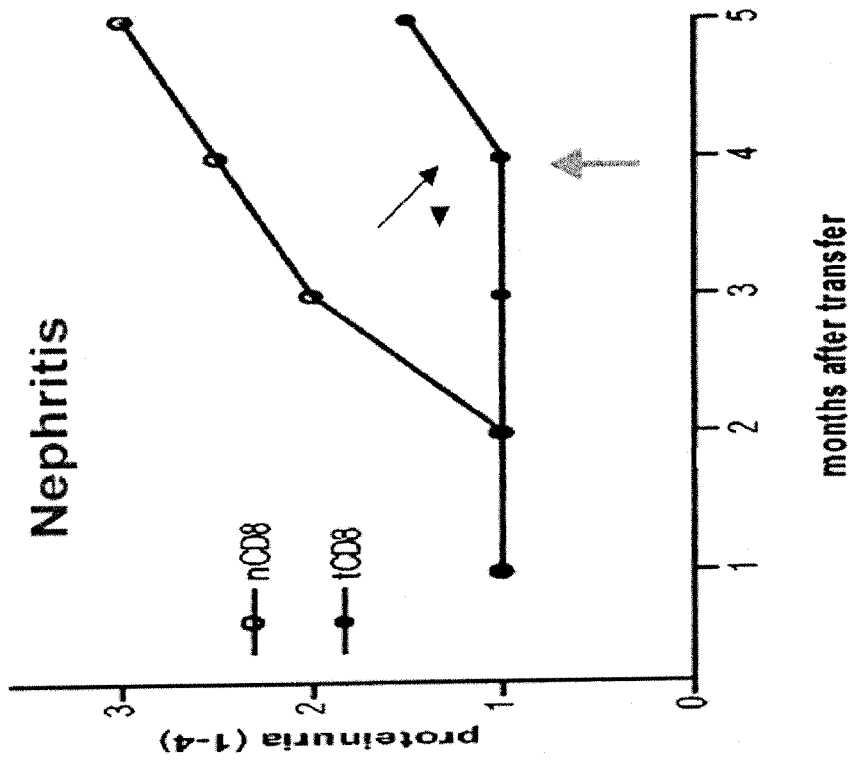

As shown in FIG. 4, the CD8+ Ti induced by i.v. administration of L-pCons are potent in suppressing nephritis and prolonging survival in vivo (see, e.g. Hahn et al., J Immunol 2005; 175:7728-37). These data represent a single transfer of $10 \times 10^6$ CD8+ T cells from spleens of tolerized mice to sublethally irradiated syngeneic recipients.

Figure 5:
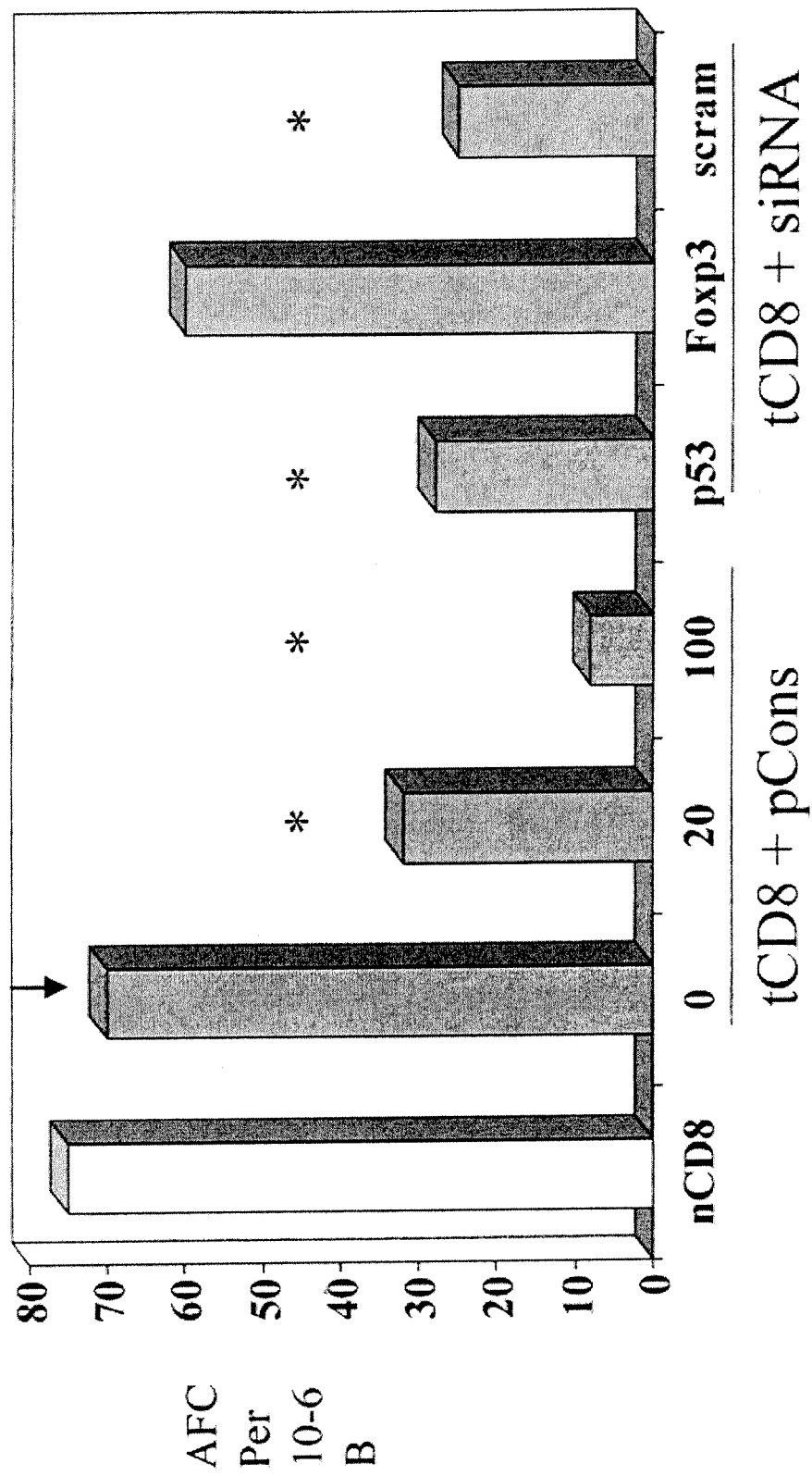
FIG. 5 provides a bar graph of data showing that the potency of CD8+ Ti cells from tolerized mice can be demonstrated in vitro in the culture assays described in Examples below. It is necessary to activate Ti suppression by adding L-pCons to the culture, and the suppression can be abrogated by silencing Foxp3 expression (via transfection with siRNA) in the Ti, but not by silencing p53 or using a scrambled siRNA in the Ti (see, e.g. Singh et al., J Immunol 2007; 178:7649-57).

As shown in FIG. 5, the potency of the CD8+ Ti from tolerized mice can be demonstrated in vitro in the culture assays described in Methods. It is necessary to activate Ti suppression by adding L-pCons to the culture, and the suppression can be abrogated by silencing Foxp3 expression (via transfection with siRNA) in the Ti, but not by silencing p53 or using a scrambed siRNA in the Ti (see, e.g. Singh et al., J Immunol 2007; 178:7649-57).

We expect several different cells capable of downregulating anti-DNA production and therefore of preventing/suppressing nephritis and improving survival in BWF1 mice treated orally with D-pCons, including the CD4+ CD25+ Foxp3+ Treg and CD8+ Foxp3+ Ti already described in the i.v. system and in addition CD4+ IL10– and/or TGFb-secreting T cells which are characteristics of oral tolerance. These cells will be searched for in the following ways: a) enumerating the surface phenotypes as well as intracellular Foxp3, TGFb, IL-10, IL-12, IL17, IFNg in the cells from spleens and mesenteric lymph nodes of mice following gavage (we expect tolerized mice compared to mice gavaged with saline to have reduced IL-12, IL-17 and IFNg which mediate SLE in BWF1 mice, and increased Foxp3, TGFb and possibly IL-10. In general TGF-beta-expressing and Foxp3-expressing cells are increased numerically in the i.v. L-pCons-treated mice, and we expect to detect them easily. Expression of IL-10 tends to be quite low (<1% of spleen cells even in tolerized mice). Therefore, to be sure to detect changes in cytokines, one can analyze mRNA by PCR technology for Foxp3 and the cytokines mentioned.

As is described in the art, one can examine the cell subsets of interest for the cytokines of interest and for Foxp3. Those subsets will include total CD4+, CD4+ CD25+, CD4+ CD25−, CD8+ CD28+, CD8+ CD28−. Since the dendritic cells that mediate oral tolerance stay within the gut wall, one typically will not search for them in the periphery.

Finally, to ensure that the cells identified are functional suppressors, one can isolate the cells of interest from tolerized vs. saline-treated mice, and study them in vitro for ability to suppress proliferation of CD4+ CD25− helper T cells as well as anti-DNA production, and in vivo for ability to delay disease, using the model shown in FIG. 4 (see, e.g. Hahn et al., Ann NY Acad Sci 2005; 1051:433-41).

Determining Whether D-pCons can Induce Regulatory T Cells in Human SLE

Figure 6:
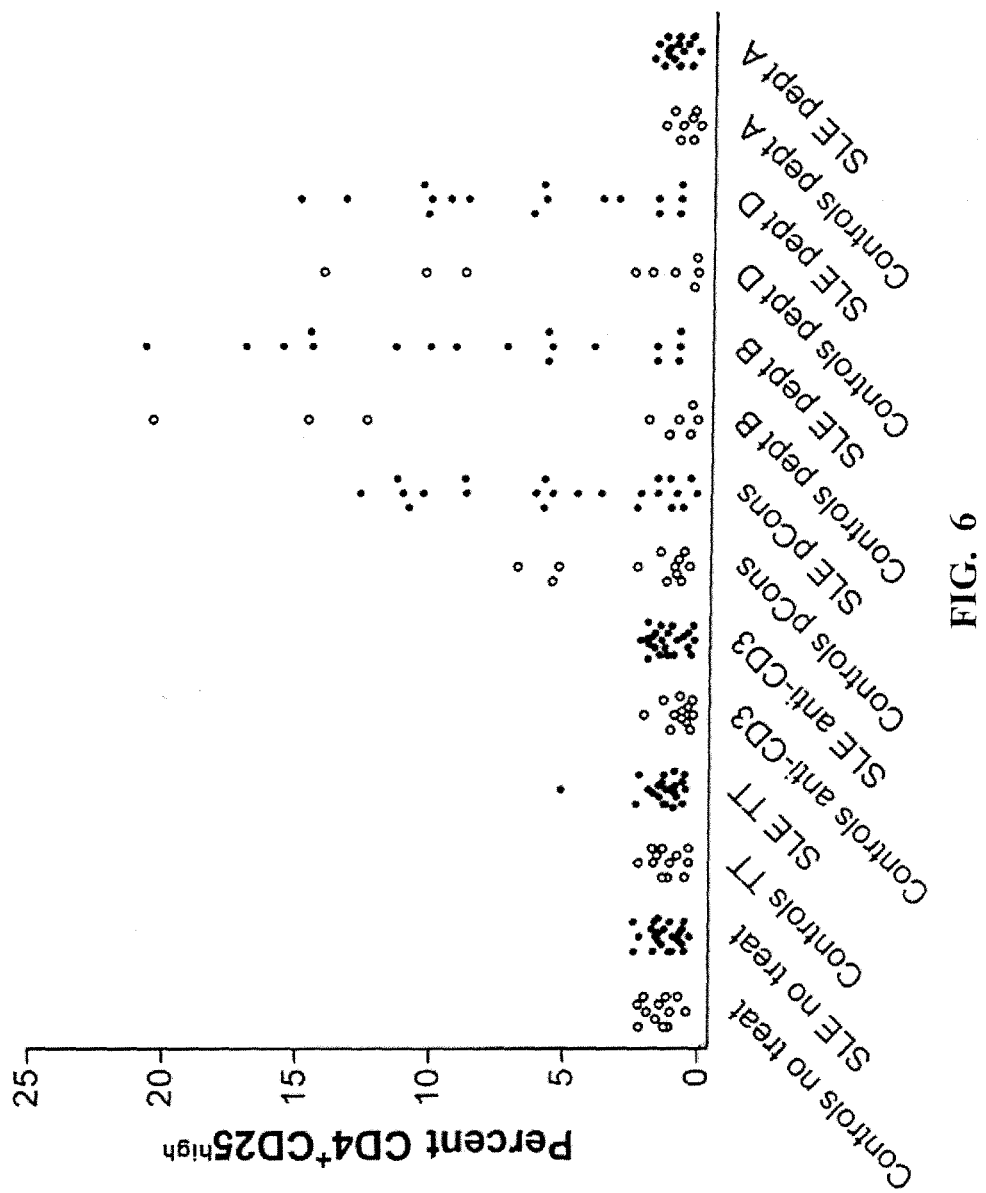
FIG. 6 shows a graph of the percentage numbers of CD4+ CD25high T cells in SLE patients and controls after 5 days in culture, data showing the ability of L-pCons to mature the CD4+ CD25hiFoxp3+ natural regulatory cells in patients with SLE. In these experiments, pCons and other stimulatory (peptides B and D) peptides and non-stimulatory peptides (peptide A) that are wild peptides from human monoclonal antibodies to DNA were incubated with peripheral blood mononuclear cells from patients with SLE. Cfsc labeling showed that the expansion seen after 5 days, and shown in the figures, was attributable to expansion of existing CD4+ CD25+ T cells and not induction of such cells de novo.
Figure 7:
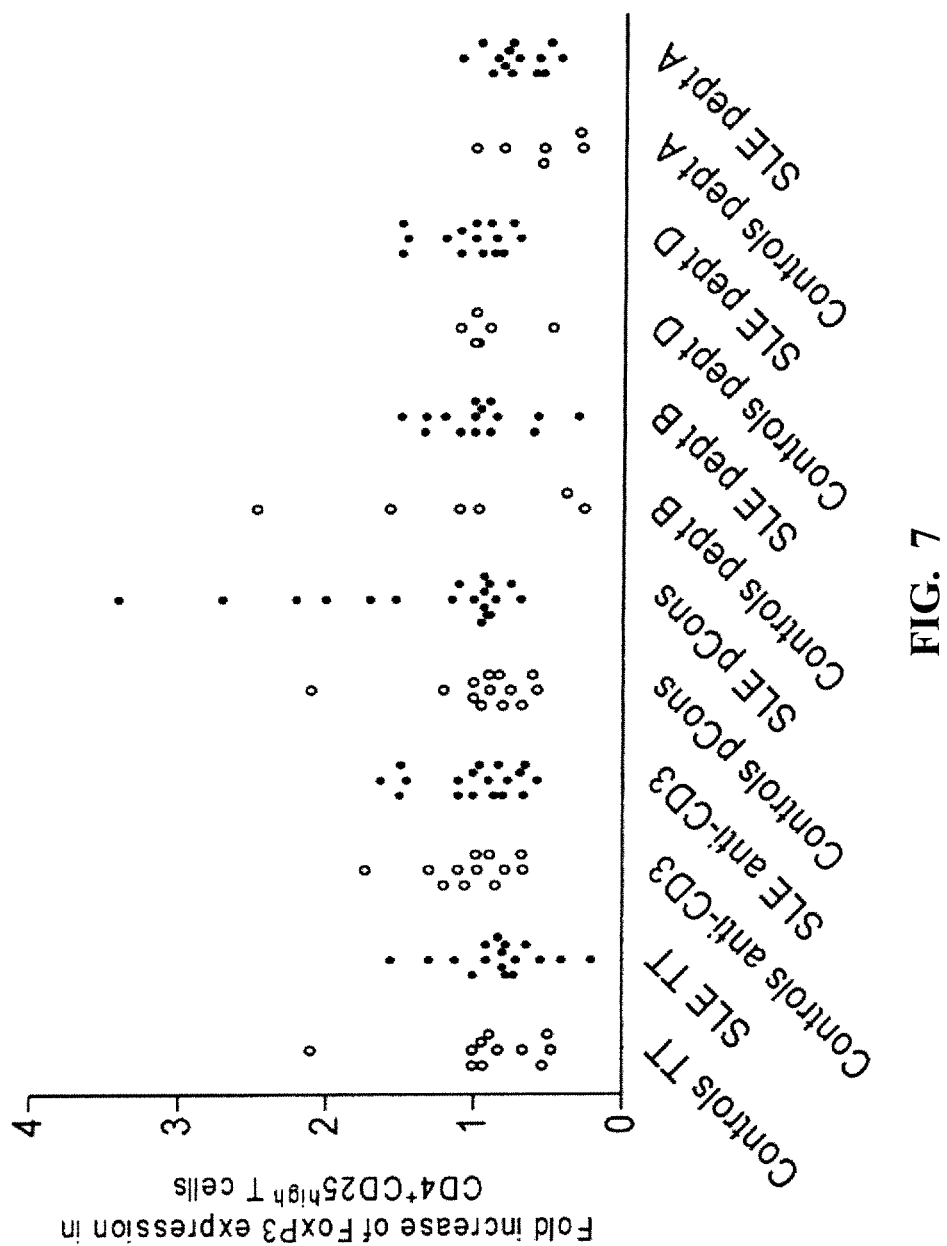
FIG. 7 shows a graph of the differences in FoxP3 expression in CD4+ CD25high T cells in SLE patient and controls after 5 days in culture, data further showing the ability of L-pCons to mature the CD4+ CD25hiFoxp3+ natural regulatory cells in patients with SLE. In these experiments, pCons and other stimulatory (peptides B and D) peptides and non-stimulatory peptides (peptide A) that are wild peptides from human monoclonal antibodies to DNA were incubated with peripheral blood mononuclear cells from patients with SLE. Cfsc labeling showed that the expansion seen after 5 days, and shown in the figures, was attributable to expansion of existing CD4+ CD25+ T cells and not induction of such cells de novo.

In FIGS. 6 and 7, we show data on the ability of L-pCons to mature the CD4+ CD25hiFoxp3+ natural regulatory cells in patients with SLE. In these experiments, pCons and other stimulatory (peptides B and D) peptides and non-stimulatory peptides (peptide A) that are wild peptides from human monoclonal antibodies to DNA were incubated with peripheral blood mononuclear cells from patients with SLE. Cfsc labeling showed that the expansion seen after 5 days, and shown in the figures, was attributable to expansion of existing CD4+ CD25+ T cells and not induction of such cells de novo. Thirteen of 23 patients showed expansion of CD4+ CD25hi cells to more than the usual 2-3% of the peripheral blood MNC, and most of those patients also overexpressed Foxp3 in those cells. Such cells are thought to be regulatory T cells. The ability to expand the cells was not confined to pCons, as expected (there is considerable degeneracy in the ability of human T cells to recognize Ig-derived peptides in patients with SLE. However the fact that L-pCons has this capacity provides evidence that it may be useful therapeutically in human SLE. Interestingly, the patients who responded with expansion of their Treg all had high titer antibody to DNA at the time the cultures were established. This may indicate a subgroup of patients likely to respond to this potential intervention.

Example 2

Suppression of Systemic Lupus Erythematosus In Vivo by Induction of Regulatory/Suppressor T Lymphocytes Following Oral or Subcutaneous Administration of an Autoantibody-Based IGG 15-Mer Peptide D Form of Pconsensus (D-Pcons)

Autoantibodies contain amino acid sequences in variable regions that are T cell epitopes and can stimulate a) helper T cells to expand autoantibody production by autologous B cells, or b) regulatory/suppressive T cells that suppress both autologous helper T and B cells. We identify several such T cell epitopes in the VH regions of several monoclonal antibodies to DNA made from NZB/NZW F1 female mice (BWF1)—a model of SLE—and from anti-DNA of several patients with SLE (see, e.g. Ebling et al., Arthritis Rheum. 1993; 36(3):355-64; and Kalsi J et al., Lupus 2004; 13:490-500). Anti-dsDNA are important in induction of nephritis in mice and some patients, and are specific markers for SLE clinically.

We administered i.v. high doses of selected stimulatory 12-to-15-mer VH peptides singly and in combination to young BWF1 mice before onset of clinical nephritis; the combination was effective in delaying anti-DNA production and nephritis and to prolong survival significantly (see, e.g. Singh et al., J Exp Med. 1995 (6):2017-27; 1995; Singh et al., J Clin Invest. 1995; 96(6):2990-6; Singh et al., J Clin Invest. 1998; 102(10):1841-9 J Exp Med. 1995; 183(4):1613-21; and Singh et al., Immunol Rev. 1998; 164:201-8). Since this increase in survival was small (6 weeks), we developed an algorithm based on 435 VH sequence peptides to create an artificial 15-mer peptide containing amino acid sequences which bind to I-Ed (one of the MHC Class II molecules in BWF1) and to be stimulatory for BWF1 T cells—which we called pConsensus or pCons. We administered the L form of pCons as a high dose i.v. tolerogen to BWF1 females once a month; this resulted in 24-week-prolongation of survival as well as significant delay in appearance of anti-DNA, anti-phospholipid, and proteinuria (Hahn et al., Arthritis Rheum. 2001 44(2):432-41). The control artificial 15-mer, pNegative (pNeg) was constructed to bind I-Ed but not stimulate T cells. FIGS. 3A and 3B respectively show: (1) the model of L-pCons and L-pNeg; and (2) the survival data for BWF1 mice treated with the two peptides.

Subsequent data show the clinical benefit of pCons in BWF1 mice result from the following factors. First, the induction of CD4+ CD25+ Foxp3 regulatory T cells (Treg) which are peptide-specific and directly suppress CD4+ CD25− helper T cells on contact (probably both via membrane-bound TGFb and GITR) as well as B cells. This results in suppression of anti-DNA production, as shown disclosed for example in La Cava et al., J.I. 2004, 173: 3542-3548. Second, the induction of CD8+ Foxp3+ non-cytotoxic suppressive T cells (Ts) which suppress directly both CD4+ CD25− helper T cells and autologous anti-DNA-secreting B cells. These Ts are peptide-specific and work at least in part via secretion of TGFb (see, e.g. Hahn et al Ann N Y Acad Sci. 2005; 1051:433-41; Singh R P et al., J. Immunol. 2007; 178(12):7649-57; and Singh et al., J. Immunol. 2008; 180(4): 2069-80). These Ts on adoptive transfer to young BWF1 mice significantly delay appearance of anti-DNA and proteinuria and significantly prolong survival, as disclosed for example in Hahn et al., J.I. 2005, 175: 7728-7737. These cells can also be induced by vaccination of BWF1 mice with DNA encoding human IgG1 and pCons (see, e.g. Ferrera et al., Ann NY Acad Sci 2007; 1110:99-111). Third, anergy in CD4+ helper T cells (See, e.g. La Cava et al., J.I. 2004, 173: 3542-3548).

Figure 8:
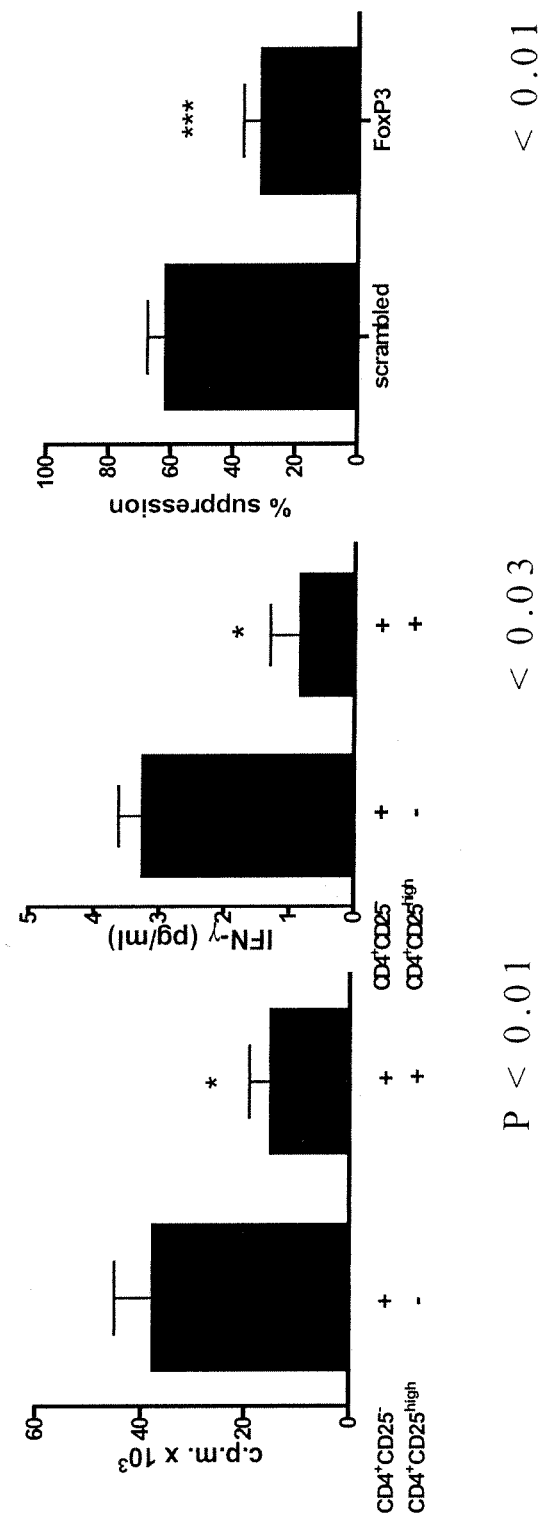
FIG. 8 provides bar graphs showing that pCons-induced Treg suppress proliferation and IFNg production by CD4+ CD25- T cells at 1:1 ratios and that this effect depends in part on Foxp3 expression. T cells were also expanded and silencing of Foxp3 by transfection with specific siRNA for Foxp3 abrogated the suppressive capacity of the induced T reg by ½ ($3^{rd}$ panel, FIG. 8).
Figure 9:
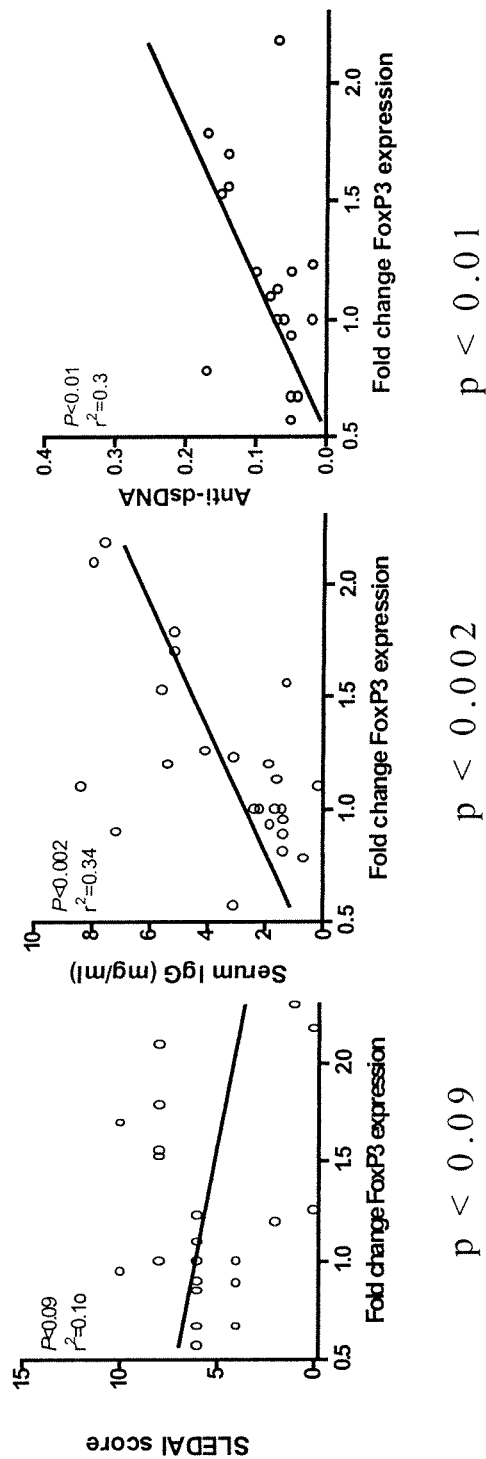
FIG. 9 shows graphs of Foxp3 expression. These graphs show that the expression of Foxp3 in CD4+ CD25+ T cells correlated positively with serum levels of IgG and of anti-dsDNA in the SLE patients, but correlation with the Selena-SLEDAI measure of disease activity was not significant (p<0.09).
Figure 10:
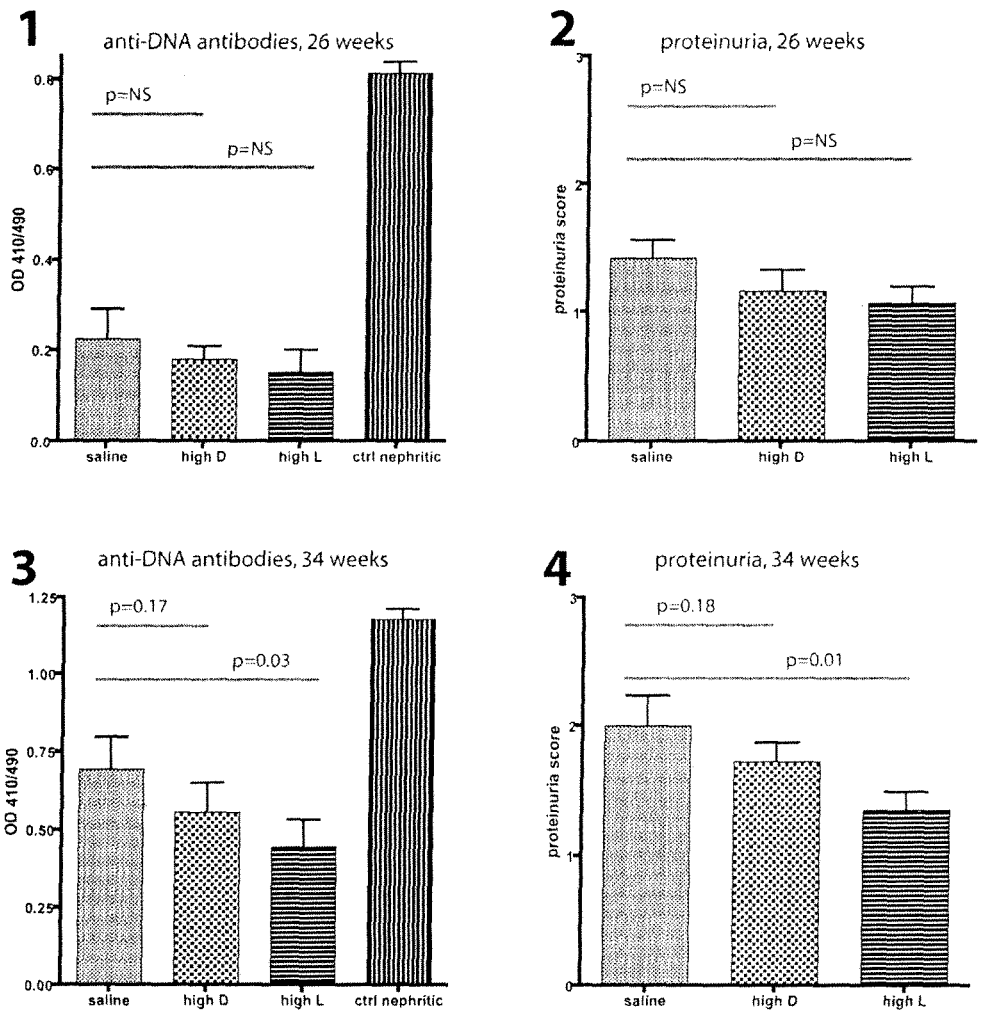
FIG. 10 shows the presence of anti-DNA antibodies (left) and proteinuria (right) in plasma of mice treated with saline, D-pCons (250 ug), and L-pCons (250 ug) at 26 (top) and 34 weeks of age (bottom). Anti-DNA antibodies were measured by ELISA and proteinuria by Azostix (see, e.g. Yang et al., J. I., 2003, 171: 2142-2153).

Next, we studied the ability of L-pCons to induce Treg in T cells from the peripheral blood of patients with SLE (36 patients, 32 healthy controls). Stimulatory control peptides B and D are wild peptides from human mAb anti-DNA; peptide A is a nonstimulatory negative control (see, e.g. Kaki et al., Lupus 2004; 13:490-500). As shown in FIG. 6, addition of pCons or peptides B and D to cultures of SLE T cells expanded CD4+ CD25hi populations in some patients (and in some controls: we have not found a stimulatory Ig peptide that is exclusively recognized by SLE patients). These expanded cells were regulatory (FIG. 8): they suppressed proliferation and IFNg synthesis by autologous CD4+ CD25− cells in culture. Numbers of CD4+ Foxp3+ T cells were also expanded and silencing of Foxp3 by transfection with specific siRNA for Foxp3 abrogated the suppressive capacity of the induced T reg by ½ ($3^{rd}$ panel, FIG. 8). Finally, as shown in FIG. 9, the expression of Foxp3 in CD4+ CD25+ T cells correlated positively with serum levels of IgG and of anti-dsDNA in the SLE patients, but correlation with the Selena-SLEDAI measure of disease activity was not significant (p<0.09). Patients who were anti-DNA negative were unlikely to respond to pCons with expansion of Treg (see, e.g. La Cava et al, Lupus. 2008; 17(5):421-5).

Lastly, we synthesized the D-form of pCons, for the purpose of administering it orally since D-forms are resistant to acid degradation. These studies show that administration of D-pCons or L-pCons subcutaneously to mice induces Treg and Ti. Specifically, studies have been completed in which BWF1 mice were fed 5 days a week out of every 30 days saline, low dose pCons (25 ug), middle dose (100 ug) or high dose (250 ug) by gavage. Both D and L-forms are being studied. Most of those mice were sacrificed to study characteristics of cells in mesenteric lymph nodes and spleens. Observations from these studies are disclosed in the following paragraphs.

First, we observed that CD8+ T cells that express Foxp3 (known to be inhibitory T cells for SLE) were induced in mesenteric nodes and spleen cells by the highest dose (250 ug) of D-peptide and by the middle dose (100 ug) and high dose of L-peptide. Thus the administration of low/middle dose D-peptide and of low dose L-peptide was not effective. Data were obtained by FACS analysis of total node populations, with percent of CD8+ Foxp3+ cells in untreated mice <1%, compared to 3-6% of total CD8+ cells in the effective doses of peptide. These changes are high enough to be clinically significant according to our earlier data with L-peptide given i.v.

We also observed changes in mRNA for pertinent cytokines. The pattern of cytokine mRNA expression established in our earlier studies that associates with ability of regulatory and suppressive T cells to suppress clinical nephritis and antibodies to DNA in BWF1 mice include: an increase in expression of Foxp3; an increase in expression of TGFb; and a decrease in expression of IFNg. After feeding mice low, medium and high doses of D- and L-forms of pCons, we found the following in mesenteric lymph nodes harvested one week after the feeding: All desired features (increase in Foxp3 and TGFb with decrease in IFNg) in mice fed high dose D-peptide (250 ug) but not in mice fed low or middle doses; and all desired features in mice fed middle and high doses of L-peptide (100 or 250 ug).

We also observed the clinical effects of feeding either D- or L-peptides at the low, medium and high doses of each. Because mRNA analysis of mesenteric lymph nodes provided evidence that high dose D-peptide would induce tolerance, we began new experiments to compare high dose (250 ug) feedings of D-peptide to the same dose of L-peptide. A control group was fed saline on the same schedule as the peptide feedings, which is daily for 5 days out of each 30 days. Each group contains 14 mice; treatment was begun at age 10 weeks. Observed effects on anti-DNA are as follows. At 24 weeks of age (first panel FIG. 8), there were trends to lower anti-DNA antibody levels in both D and L peptide groups. Differences did not reach statistical significance. However, at 34 weeks (third panel FIG. 8), with anti-DNA rising higher in the saline groups, ANOVA analysis showed statistically significant differences (p<0.01), with anti-DNA in L-peptide significantly lower than saline group p<0.05 by Tukey's analysis. One-tailed t test analysis of data showed L-peptide significantly lower than saline (p=0.03) and D-peptide borderline (p=0.17 by one-tailed t test). Note that the saline control group is lower than the positive control anti-DNA, which is serum from BWF1 mice with heavy proteinuria and imminent death. Thus, the saline control has not reached the expected high level at this point but should do so in the next 2 months.

Observed effects on Proteinuria are as follows. At 24 weeks of age (panel 2 in figures below), there are no differences in mean level of proteinuria (measured as zero to 4+ using Azostix) in mice in any of the treatment groups. However, at 34 weeks (panel 4 in figures below), proteinuria is lower in the L-peptide group (p=0.01) and lower in the D-peptide group (p=0.18).

The disclosure provides evidence that the administration of D-pCons or L-pCons orally to patients with SLE who have anti-DNA antibodies will induce Treg and Ti, and those cells will be potent enough to suppress anti-DNA production and disease activity, thus making D-pCons a useful therapeutic. This disclosure therefore provides evidence that it can be used to reduce disease activity and to prevent flares after activity is reduced. The disclosed data establishes that high doses of D-peptide are effective.

The invention claimed is:

1. A composition comprising a peptide having the sequence: FIEWNKLRFRQGLEW (SEQ ID NO: 1), wherein at least one amino acid moiety is a D-amino acid.

2. The composition of claim 1, wherein 14 amino acid moieties are D-amino acids.

3. The composition of claim 1, further comprising a pharmaceutically acceptable carrier used in orally administered medications.

4. The composition of claim 1, wherein the D-amino acid peptide is coupled to a heterologous amino acid sequence.

5. A method of binding a D-amino acid peptide having the sequence: FIEWNKLRFRQGLEW (SEQ ID NO: 1) to a T lymphocyte, the method comprising:
  combining the peptide with the T lymphocyte; and
  allowing the peptide to bind the T lymphocyte so that the peptide is bound to the T lymphocyte.

6. The method of claim 5, wherein the method is used to identify the T lymphocyte as a CD4+CD25− helper T lymphocyte.

7. The method of claim 5, wherein the binding of the peptide to the T lymphocyte comprises an assay for screening the presence or susceptibility of a mammal to an immunological disorder, the assay comprising:
  labeling the peptide with a detectable label;
  incubating the labelled peptide with the T cells so that the labelled peptide is bound to the T cells; and
  observing the amount of peptide bound cells, wherein the extent of the binding of the peptide to the T cells is correlated to the presence or susceptibility to the disorder.

8. The method of claim 7, wherein the disorder comprises the production of autoantibodies.

9. The method of claim 5, wherein the method is performed in vitro.

10. A method of inhibiting the production of autoantibodies that bind double stranded DNA in a mammal, the method comprising administering to the mammal an isolated D-amino acid peptide comprising the sequence: FIEWNKL-RFRQGLEW (SEQ ID NO: 1), wherein the isolated peptide:
  binds to Major Histocompatibility Complex polypeptides expressed by T cells in the mammal; and
  inhibits the production of autoantibodies that bind double stranded DNA in the mammal.

11. The method of claim 10, wherein the mammal suffers from an autoimmune disorder comprising systemic lupus erythematosus (SLE).

12. The method of claim 10, wherein the mammal suffers from an autoimmune disorder comprising nephritis.

13. The method of claim 10, wherein the D-amino acid peptide is coupled to a heterologous amino acid sequence.

14. The method of claim 13, wherein the heterologous amino acid sequence comprises a constant region from an immunoglobulin.

15. The method of claim 10, wherein the D-amino acid peptide is administered orally.

16. The method of claim 15, wherein the D-amino acid peptide is combined with a pharmaceutically acceptable carrier comprising a composition that inhibits acidic or enzymatic degradation of the peptide.

17. The method of claim 10, wherein the administration of the D-amino acid peptide results in an induction of CD4+ CD25+Foxp3+ T cells or CD8+Foxp3+ T cells in the mammal.

18. The method of claim 10, wherein the administration of the D-amino acid peptide reduces the number of the mammal's splenic B cells that make antibodies that bind double stranded DNA by at least about 50%.

19. The method of claim 10, wherein the administration of the D-amino acid peptide results in a decrease in the concentration of proteins present in the urine of the mammal.

20. A kit, comprising a container and, within the container, an isolated D-amino acid peptide comprising the sequence: FIEWNKLRFRQGLEW (SEQ ID NO: 1), wherein the peptide is capable of binding a T lymphocyte.

* * * * *

UNITED STATES PATENT AND TRADEMARK OFFICE
CERTIFICATE OF CORRECTION

| | | |
|---|---|---|
| PATENT NO. | : 8,492,347 B2 | Page 1 of 1 |
| APPLICATION NO. | : 12/682759 | |
| DATED | : July 23, 2013 | |
| INVENTOR(S) | : Hahn et al. | |

It is certified that error appears in the above-identified patent and that said Letters Patent is hereby corrected as shown below:

In the Specification
Column 1

Lines 14-17, delete the text, "This invention was made with United States Government support under Grant No. AI346776 awarded by the National Institutes of Health. The Government has certain rights in this invention."

and insert the text, --This invention was made with Government support under Grant No. AI346776 awarded by the National Institutes of Health. The Government has certain rights in the invention.--

Signed and Sealed this
Twenty-fifth Day of March, 2014

Michelle K. Lee
*Deputy Director of the United States Patent and Trademark Office*